United States Patent [19]

Yamada et al.

[11] Patent Number: 4,550,078
[45] Date of Patent: Oct. 29, 1985

[54] METHOD FOR THE QUANTITATIVE DETERMINATION OF INDIVIDUAL POLYAMINE COMPONENTS IN A MIXTURE

[75] Inventors: Hideaki Yamada, Kyoto; Shogo Otsuji, Kagoshima; Kimiyasu Isobe, Konan; Kuniyoshi Matsunaga, Ichinomiya; Tadahiko Inukai, Nagoya, all of Japan

[73] Assignee: Amano Seiyaku Kabushiki Kaisha, Aichi, Japan

[21] Appl. No.: 495,677

[22] Filed: May 18, 1983

[30] Foreign Application Priority Data

Sep. 14, 1982 [JP] Japan ................................ 57-158848

[51] Int. Cl.$^4$ ............................................. C12Q 1/26
[52] U.S. Cl. ......................................... 435/25; 435/28
[58] Field of Search .................................... 435/25, 28

[56] References Cited
PUBLICATIONS

Mashige et al.–Chem. Abst., vol. 99, (1983), p. 66973v, (abstract of 1981 article).

Isobe et al.–Chem. Abst., vol. 94, (1981), p. 188,129s.

*Primary Examiner*—Sam Rosen
*Attorney, Agent, or Firm*—Brisebois & Kruger

[57] ABSTRACT

A rapid and reliable method is proposed for the quantitative determination of the individual free and acetylated polyamines, i.e. spermine, spermidine, putrescine, acetylspermine, $N^1$- and $N^8$-acetylspermidines and acetylputrescine in the body fluid of a patient suffering cancer or other deseases to facilitate diagnosis and therapeutic treatment. The method comprises subjecting the aqueous fluid to several enzymatic oxidative decomposition reactions of the polyamines in sequence or in combination by use of the 4 enzymes, i.e. polyamine oxidase AT-1, polyamine oxidase PC-3, putrescine oxidase and acetylputrescine oxidase, and determining, preferably photometrically, the amount of hydrogen peroxide formed as a byproduct in each of the reaction steps followed by setting up a set of simultaneous equations to give the respective amounts of the individual polyamines as a function of the amounts of the hydrogen peroxide formed in the reaction steps and solving the simultaneous equations.

10 Claims, 3 Drawing Figures

METHOD FOR THE QUANTITATIVE DETERMINATION OF INDIVIDUAL POLYAMINE COMPONENTS IN A MIXTURE

BACKGROUND OF THE INVENTION

The present invention relates to a method for the quantitative determination of individual polyamine components, i.e. free polyamines and acetylated polyamines, in an aqueous mixture or, more particularly, to a method for the quantitative determination of individual contents of polyamine components in an aqueous mixture containing at least two of the polyamines selected from the group consisting of free polyamines, e.g. spermine, spermidine and putrescine, and acetylated polyamines, e.g. acetylspermine, $N^1$-acetylspermidine, $N^8$-acetylspermidine and acetylputrescine, including at least one of the said acetylated polyamines by an enzymatic means.

As is well known, polyamines or, in particular, free polyamines such as putrescine $NH_2(CH_2)_4NH_2$, spermidine $NH_2(CH_2)_4NH-(CH_2)_3NH_2$ and spermine $NH_2(CH_2)_3NH(CH_2)_4NH(CH_2)_3NH_2$ are widely found in almost all kinds of living bodies as a constituent of the cells not only in animals but also in plants and microorganisms and pertain to the division and multiplication of cells as well as the metabolism of nucleic acid as a biochemical background thereof.

It has been reported recently that the concentration of the polyamines in urine is larger from the patients of cancer than from healthy persons (Cancer Research, volume 31, pages 1555–1558) and investigations have been undertaken extensively by many investigators on the relationship between the contents of polyamines in the so-called body fluids such as urine, blood, limph and the like of a patient and the condition of cancer which the patient suffers. It is now understood that the polyamine metabolism is stimulated in the increasing period of the tumor tissues and fluctuation in the amount of polyamine excretion may be taken as a reflection of the transition of the condition of a patient suffering cancer so that it is eagerly desired to develop a rapid and convenient method for the quantitative determination of polyamine constituents in a sample taken from a patient of cancer as important information for the clinical diagnosis of cancer as well as for the therapeutic effect therefor.

Conventionally several methods have been undertaken for the purpose of quantitative determination of polyamines including a gas chromatographic method (see, for example, Clinical Chemistry, volume 19, pages 904–907), a method by use of an amino acid analyzer (see, for example, FEBS Letters, volume 46, pages 305–307) and a method of high-speed liquid chromatography (see, for example, Journal of Chromatography, volume 145, pages 141–146). These chemical methods constituting the major current of the analytical methods for polyamines are not quite satisfactory from the practical standpoint because these methods cannot be performed with sufficient rapidness and the procedures of these methods are complicated and lengthy due to the necessity of pretreatment to convert the polyamines into derivatives susceptible to the determination in the respective methods with different principles.

Alternatively, several enzymatic methods also have been proposed for the determination of polyamines by utilizing the specific activity of a particular enzyme including a method for the free polyamines (see, for example, Japanese Patent Publication No. 56-36918), a method for the determination of spermidine and spermine (see, for example, Japanese Patent Publication No. 56-21398) and a method for the determination of spermine, spermidine and putrescine (see, for example, Japanese Patent Kokai No. 50-9492). These enzymatic methods are preferred to the above mentioned chemical methods because the troublesome pretreatment can be omitted for the conversion of the polyamines into the derivatives suitable for the determination.

According to the results of recent investigations, on the other hand, it is important in order to understand the condition of the patient of cancer to know not only the total amount of the polyamines but also the proportion of the respective free polyamines, i.e. spermidine, spermine and putrescine, as well as the proportion of the acetylated polyamines, for example, the proportion of acetylspermine, acetylspermidine and acetylputrescine or the proportion of $N^1$-acetylspermidine and $N^8$-acetylspermidine, while the above-mentioned enzymatic methods for the analysis are not suitable for the direct determination of the acetylated polyamines because the methods are for the free polyamines and the acetylated polyamines must be deacetylated to the corresponding free polyamines by the hydrolysis reaction with hydrochloric acid and the like or by an enzymatic method. Therefore, it has been eagerly desired to develop a rapid and convenient method for the quantitative determination of the individual polyamine components in a mixture containing not only free polyamines but also acetylated polyamines capable of giving very reliable results.

SUMMARY OF THE INVENTION

It is therefore an object of the present invention to provide a novel and improved method for the quantitative determination of the individual polyamine components in an aqueous mixture containing free polyamines and acetylated polyamines capable of rapidly and conveniently giving very reliable results.

The method of the present invention for the quantitative determination of the individual polyamines is applicable to an aqueous mixture containing at least two of the polyamines selected from the group consisting of the free polyamines, i.e. spermine, spermidine and putrescine, and acetylated polyamines, i.e. acetylspermine, $N^1$-acetylspermidine, $N^8$-acetylspermidine and acetylputrescine, including at least one of the abovementioned acetylated polyamines.

The method of the present invention utilizes the principle that certain enzymes are specific for the enzymatic oxidative decomposition of the respective polyamines yielding hydrogen peroxide as a byproduct of the reaction so that the amounts of the individual polyamines in the polyamine mixture can be determined by the determination of the amounts of hydrogen peroxide produced in the respective enzymatic reactions undertaken successively or separately with a particular enzyme or under particular conditions for the enzymatic reaction.

Thus, the method of the present invention comprises the steps of:

(a) subjecting the aqueous mixture containing at least two of the polyamines including at least one acetylated polyamine to at least two enzymatic oxidative decomposition reactions successively or separately, the number of the reaction steps being the same as or larger than the number of the polyamines in the mixture, each by use of an oxidation enzyme selected from the group consisting of polyamine oxidases, putrescine oxidase and acetylputrescine oxidase, the kind of the enzyme or the conditions of the reaction being effective for the enzymatic oxidative decomposition of one or two of the polyamines but ineffective for the other polyamine components, to form hydrogen peroxide as a byproduct in the enzymatic oxidative decomposition reaction, (b) determining the amount of the hydrogen peroxide formed in each step of the enzymatic oxidative decomposition reactions, (c) setting up a set of simultaneous equations each giving the amount of the hydrogen peroxide formed in each of the enzymatic oxidative decomposition reactions as a function of the contents of the individual polyamine components in the aqueous mixture decomposed in the reaction, and (d) solving the simultaneous equations in terms of the respective contents of the individual polyamine components in the aqueous mixture.

DETAILED DESCRIPTION OF THE PREFERRED EMBODIMENTS

As is described above, the method of the present invention is applicable to an aqueous mixture containing, as the substrates of the enzymatic reactions, at least two polyamines selected from 7 kinds of free and acetylated polyamines including spermine, spermidine and putrescine as the free polyamines and acetylspermine, $N^1$-acetylspermidine, $N^8$-acetylspermidine and acetylputrescine as the acetylated polyamines. The mixture should contain at least one of the acetylated polyamines.

The oxidation enzymes having specific activity on the above mentioned substrates, on the other hand, include polyamine oxidases which may be polyamine oxidase AT-1 or polyamine oxidase PC-3, putrescine oxidase and acetylputrescine oxidase. Following are the descriptions for the characterization of these 4 enzymes.

(A) Polyamine oxidase AT-1

This enzyme is known as described, for example, in Japanese Patent Kokai 56-92788. The properties thereof are as follows.

(1) Enzymatic activity: active on spermidine to produce each 1 mole of putrescine, 3-aminopropanal and hydrogen peroxide per mole of the substrate; and active on spermine to produce 1 mole of putrescine and each 2 moles of 3-aminopropanal and hydrogen peroxide per mole of the substrate (2) Substrate specificity: active on spermidine and spermine to oxidize them with formation of hydrogen peroxide as a byproduct with an oxidation ratio of spermidine to spermine of about 2:1

(3) Optimum pH: around 6.5

(4) pH stability: at least 90% of remaining activity after being kept standing at 30° C. for 30 minutes with a pH of 5.2–6.5

(5) Optimum temperature: around 45° C. at pH 6.5 and around 50° C. at pH 7.0

(6) Temperature stability: at least 90% remaining activity after being kept standing at 30° C. for 30 minutes with a pH of 6.5

(7) Absorption spectrum: maximum absorption at about 375 nm and 460 nm characteristic in flavin enzymes (8) Inhibitors: strong inhibition by metallic ions, in particular, silver and mercury ions (9) pH at isoelectric point: 5.0–5.25

(10) Molecular weight: 130,000 by the gel filtration method with Sephadex G-200

(11) Molecular weight of subunits: 65,000 by the method of SDS disc electrophoresis (12) Crystalline form: needle-like (B) Polyamine oxidase PC-3

This enzyme is known as described, for example, in Japanese Patent Kokai 56-92789. The properties thereof are as follows. (1) Enzymatic activity: active on spermidine to produce each 1 mole of putrescine, 3-aminopropanal and hydrogen peroxide per mole of the substrate; and active on spermine to produce 1 mole of putrescine and each 2 moles of 3-aminopropanal and hydrogen peroxide per mole of the substrate (2) Substrate specificity: active on spermidine and spermine but almost inactive on the other polyamines (3) Optimum pH: optimum activity on spermidine at around pH 5.0 and on spermine at around pH 9.5

(4) pH stability: at least 85% of remaining activity on each of spermidine and spermine after being kept standing at 30° C. for 10 minutes with a pH of 3.0–5.0

(5) Optimum temperature: around 25° C. for spermidine with pH 6.5; and around 35° C. and 40° C. for spermine with pH 6.5 and 7.0, respectively (6) Temperature stability: at least 95% of remaining activity after being kept standing at 35° C. for 10 minutes with pH 4.0 and at least 85% of remaining activity after being kept standing at 20° C. for 10 minutes with pH 7.0 for spermine as the substrate (7) Absorption spectrum: maximum adsorption at about 375 nm and 450 nm characteristic in flavoproteins, accompanied by 2 moles of FAD per mole of the enzyme (8) Inhibitors: inhibition by PCMB, monoiodoacetic acid, silver and mercury ions and the like for spermine as the substrate and inhibition by silver and aluminum ions for spermidine as the substrate (9) pH at isoelectric point: 5.4–5.6

(10) Molecular weight: 160,000 by the gel filtration method with Sephadex G-200

(11) Molecular weight of subunits: 80,000 by the method of SDS disc electrophoresis (12) Crystalline form: needle-like (C) Putrescine oxidase This enzyme is known as described, for example, in Agricultural Biological Chemistry, volume 30, page 1202. The properties thereof are as follows.

(1) Enzymatic activity: active on putrescine to produce each 1 mole of 4-aminobutanal, hydrogen peroxide and ammonia per mole of the substrate; and active on spermidine to produce each 1 mole of 1,3-diaminopropane, 4-aminobutanal and hydrogen peroxide per mole of the substrate (2) Substrate specificity: active on spermidine and putrescine but inactive on spermine, 1,3-diaminopropane and acetylated polyamines (3) Optimum pH: around 8.5

(4) pH stability: at least 90% of remaining activity after being kept standing at 40° C. for 10 minutes with a pH of 5.5–10.0

(5) Optimum temperature: about 55° C. (6) Temperature stability: at least 90% of remaining activity after being kept standing at 45° C. for 10 minutes with a pH of 7.0

(7) Absorption spectrum: maximum adsorption at about 380 nm and 460 nm, containing FAD as a prosthetic group (8) pH at isoelectric point: 4.1

(9) Molecular weight: about 90,000

(D) Acetylputrescine oxidase

This enzyme is a novel enzyme not described in any literatures and produced by *Aspergillus oryzae* IAM 2682. This enzyme can be prepared, for example, by the following procedure. Thus, a nutrient medium containing 0.25% of acetylputrescine, 0.1% of dipotassium phosphate $K_2HPO_4$, 0.15% of potassium dihydrogenphosphate $KH_2PO_4$ and 0.02% of magnesium sulfate $MgSO_4.7H_2O$ and having a pH of about 5.5 is inoculated with *Aspergillus oryzae* IAM 2682 which is cultured for 1 to 2 days under an aerobic condition. The fungus body thus obtained is subjected to extraction to give a crude extract solution containing acetylputrescine oxidase which is further purified by a combination of known purification methods including column chromatographic methods by use of DEAE-cellulose, hydroxyapatite, Sephadex G-200 and the like adsorbents and salting-out with ammonium sulfate. The purified enzyme is pure by the assay of disk electrophoresis.

The properties thereof are as follows.

(1) Enzymatic activity: active on acetylputrescine to produce each 1 mole of 4-acetylaminobutanal, ammonia and hydrogen peroxide per mole of the substrate (2) Substrate specificity: active on acetylputrescine but inactive on free polyamines and acetylated polyamines other than acetylputrescine (3) Optimum pH: around 8

(4) pH stability: at least 85% of remaining activity after being kept standing at 37° C. for 30 minutes with a pH of 6.0–8.5

(5) Optimum temperature: about 50° C. with a pH of 7.5

(6) Temperature stability: at least 90% of remaining activity after being kept standing at 40° C. for 30 minutes with a pH of 7.0

(7) Specific constituent: copper (8) pH at isoelectric point: around 5.0

Following are the reaction schemes for the enzymatic oxidation decomposition of different substrates by each of the above-mentioned enzymes.

I. Decomposition reaction of free polyamines by polyamine oxidase AT-1

It should be noted that, although polyamine oxidase AT-1 is active only on spermine and spermidine when the concentration thereof is low, the enzyme is also active on acetylspermine and $N^1$-acetylspermidine when the concentration of the enzyme is increased.

Similarly, polyamine oxidase PC-3 is active also on $N^8$-acetylspermidine in addition to spermine and spermidine provided that the concentration of the enzyme is relatively high.

Table 1 below is a tabulation of the specific combinations of each of the enzymes with particular substrates in which the activity of the enzyme is exhibited for the oxidative decomposition of the substrate specifying the amounts of the relevant decomposition products, i.e. hydrogen peroxide and polyamines, in moles per mole of the substrate, to help understanding of the following description.

TABLE 1

| | Enzyme | | | |
|---|---|---|---|---|
| Substrate | Polyamine oxidase AT-1 | Polyamine oxidase PC-3 | Putrescine oxidase | Acetyl-putrescine oxidase |
| Spermine | 1 mole of putrescine, 2 moles of $H_2O_2$ | 1 mole of putrescine, 2 moles of $H_2O_2$ | — | — |
| Spermidine | 1 mole of putrescine, 1 mole of $H_2O_2$ | 1 mole of putrescine, 1 mole of $H_2O_2$ | 1 mole of $H_2O_2$ | — |
| Putrescine | — | — | 1 mole of $H_2O_2$ | — |
| Acetyl-spermine* | 1 mole of putrescine, 2 moles of $H_2O_2$ | — | — | — |
| $N^1$—Acetyl-spermidine* | 1 mole of putrescine, 1 mole of $H_2O_2$ | — | — | — |
| $N^8$—Acetyl-spermidine* | — | 1 mole of acetyl-putrescine, 1 mole of $H_2O_2$ | — | — |
| Acetyl-putrescine | — | — | — | 1 mole of $H_2O_2$ |

*The activity of the enzyme on the substrate is exhibited only with a relatively high concentration of the enzyme.

Thus, the principle of the inventive method is obtaining solutions of a set of simultaneous equations each set up for the amount of the hydrogen peroxide formed as a product in each step of the enzymatic oxidative decomposition reactions of the polyamine mixture with one of the specified enzymes undertaken successively or separately, in which one or two of the possible enzymatic reactions for the 10 combinations of the enzyme and substrate tabulated in Table 1 have taken place, as a function of the respective contents of the 7 individual polyamine components.

Better understanding of the inventive method will be given by the following explanation for several typical or preferable embodiments of the method. In the following description, the amount or activity of each of the enzymes is given in "units", where the amount of the enzyme sufficient to produce 1 $\mu$mole of hydrogen peroxide for 1 minute is taken as one unit when the enzymatic reaction is performed according to the procedure described below.

(A) Activity determination of polyamine oxidase AT-1

A coloring solution is prepared by dissolving 10 mg of 4-aminoantipyrine, 0.2 ml of phenol and 5 mg of peroxidase (a product by Boehringer Mannheim GmbH, Grade II) in 100 ml of a 0.1M phosphate buffer solution of pH 6.5 and 1.5 ml of this coloring solution is admixed with 0.5 ml of a 10 mM solution of spermidine followed by preheating of the mixture at 35° C. for 3 minutes. Thereafter, 0.5 ml of the enzyme solution is added thereto to effect the enzymatic reaction resulting in coloration of the solution due to the formation of hydrogen peroxide and the increment of the absorbance at 505 nm is measured at a moment 1 minute after the addition of the enzyme solution. The amount of the hydrogen peroxide is calculated from this value of the absorbance with 6250 as the molecular extinction coefficient.

(B) Activity determination of polyamine oxidase PC-3

The activity of the enzyme is determined in just the same manner as in (A) above for the activity determination of polyamine oxidase AT-1 excepting the use of 0.5 ml of a 10 mM solution of spermine as the substrate in place of the spermidine solution.

(C) Activity determination of putrescine oxidase

The activity of the enzyme is determined in just the same manner as in (A) above for the activity determination of polyamine oxidase AT-1 excepting the use of 0.5 ml of a 10 mM solution of putrescine as the substrate in place of the spermidine solution and the use of a 0.1M borate buffer solution having a pH of 8.5 in place of the phosphate buffer solution in the preparation of the coloring solution.

(D) Activity determination of acetylputrescine oxidase

The activity of the enzyme is determined in just the same manner as in (A) above for the activity determination of polyamine oxidase AT-1 excepting the use of 0.5 ml of a 10 mM solution of acetylputrescine as the substrate in place of the spermidine solution and the use of a 0.1M phosphate buffer solution of pH 7.5 in place of the buffer solution of pH 6.5 in the preparation of the coloring solution.

In the first of the preferable embodiments of the inventive method, an aqueous mixture containing the 7 polyamine components, i.e. spermine, spermidine, putrescine, acetylspermine, $N^1$-acetylspermidine, $N^8$-acetylspermidine and acetylputrescine, is subjected to the enzymatic oxidative decomposition reactions by use of either one of the above described 4 enzymes according to the following procedure including 7 steps $A_1$ to $G_1$ successively or separately and the amount of the hydrogen peroxide produced in each of the steps is determined, preferably, spectrophotometrically. Following description is given on an assumption that the spectrophotometric determination is performed with 2.5 ml volume of the sample solution.

Step $A_1$:

A volume of the aqueous mixture is subjected to the enzymatic oxidative decomposition by use of 0.02–0.20 unit of polyamine oxidase AT-1 per 2.5 ml of the aqueous mixture at a pH of 5–7 or, preferably, 6–6.5 and the amount of hydrogen peroxide is determined after complete oxidation of spermine and spermidine contained in the aqueous mixture. Assume that the amount of the thus produced hydrogen peroxide is equal to $A_1$ moles, $A_1$ being equal to the summation of the numbers of moles of twice of the amount of spermine and the amount of spermidine. Besides, putrescine is produced in this step each in an equimolar amount from the spermine and spermidine. Step $B_1$:

The aqueous mixture after the step $A_1$ is admixed with a small amount of alkali to have a pH of 7–9 or, preferably, 8-8.5 and at least 1 unit of putrescine oxidase is added thereto to effect the enzymatic oxidation of putrescine. The amount of hydrogen peroxide after complete oxidation is determined. Assume that the amount of the hydrogen peroxide is equal to $B_1$ moles, $B_1$ being equal to the summation of the numbers of moles of the putrescine contained in the starting aqueous mixture and the putrescine produced by the reaction in the step $A_1$. Note that the number of moles of putrescine produced in the step $A_1$ is equal to the total number of moles of spermine and spermidine in the starting aqueous mixture.

Step $C_1$:

Another portion of the starting aqueous mixture is admixed with at least 1 unit of polyamine oxidase AT-1 to effect the enzymatic oxidation of spermine, spermidine, acetylspermine and $N^1$-acetylspermidine at a pH of 5-7 or, preferably, 6-6.5 and the amount of hydrogen peroxide produced in the reaction is determined after completion of the reaction. Assume that the thus determined amount of the hydrogen peroxide is equal to $C_1$ moles, $C_1$ being equal to the summation of the numbers of moles of the spermidine and $N^1$-acetylspermidine and each twice of the numbers of moles of the spermine and acetylspermine contained in the starting aqueous mixture. Besides, putrescine is produced each in an equimolar amount from the respective polyamines. Step $D_1$:

The pH of the aqueous mixture after the step $C_1$ above is adjusted to 7-9 or, preferably, 8-8.5 and at least 1 unit of putrescine oxidase is added thereto to effect the enzymatic oxidation reaction of the putrescine. The amount of hydrogen peroxide is determined after completion of the reaction. Assume that the thus determined amount of the hydrogen peroxide is equal to $D_1$ moles, $D_1$ being equal to the summation of the numbers of moles of the putrescine contained in the starting aqueous mixture and produced by the reaction in the step $C_1$ above. Note that the number of moles of the amount of putrescine produced in the step $C_1$ is equal to the summation of the numbers of moles of the 4 polyamine components decomposed in the step $C_1$. Step $E_1$:

A further portion of the starting aqueous mixture is admixed with at least 1 unit of putrescine oxidase and the enzymatic oxidation of spermidine and putrescine contained therein is effected at a pH of 7-9 or, preferably, 8-8.5. Assume that the amount of hydrogen peroxide determined after completion of the reaction is equal to $E_1$ moles, $E_1$ being equal to the summation of the numbers of moles of the spermidine and putrescine in the starting aqueous mixture. Step $F_1$:

The aqueous mixture after the step $E_1$ above is further admixed with 0.05-0.5 unit of acetylputrescine oxidase to effect the enzymatic oxidation of acetylputrescine contained therein and the amount of hydrogen peroxide is determined after completion of the reaction. Assume that the thus determined amount of the hydrogen peroxide is equal to $F_1$ moles, $F_1$ being equal to the number of moles of the acetylputrescine contained in the starting aqueous mixture.

Step $G_1$:

The pH of the aqueous mixture after the step $F_1$ above is adjusted to about 5-5.5 and at least 3 units of polyamine oxidase PC-3 are added thereto to effect the enzymatic oxidation of the spermine and $N^8$-acetylspermidine into putrescine and acetylputrescine, respectively, together with formation of hydrogen peroxdie each in an equimolar amount from these two substrates. Assume that the amount of the hydrogen peroxide determined after completion of the reaction is equal to $G_1$ moles, $G_1$ being equal to the summation of the numbers of moles of the $N^8$-acetylspermidine and twice amount of the spermine in the aqueous mixture. Meanwhile, the putrescine oxidase and acetylputrescine oxidase previously added to the aqueous mixture in the steps $E_1$ and $F_1$, respectively, are almost inactive under the above mentioned condition of pH undertaken in this step.

Having obtained the numbers of moles $A_1$, $B_1$, $C_1$, $D_1$, $E_1$, $F_1$ and $G_1$ of the hydrogen peroxide produced in the respective steps $A_1$ to $G_1$ above, following set of simultaneous equations can be set up each for one of $A_1$ to $G_1$ as a function of the amounts of the relevant polyamine components in moles in the aqueous mixture, in which $X^1$, $X^2$, $X^3$, $X^4$, $X^5$, $X^6$ and $X^7$ each denote the amount of spermine, spermidine, putrescine, acetylspermine, $N^1$-acetylspermidine, $N^8$-acetylspermidine and acetylputrescine in moles, respectively:

$A_1 = 2X^1 + X^2$;
$B_1 = X^1 + X^2 + X^3$;
$C_1 = 2X^1 + X^2 + 2X^4 + X^5$;
$D_1 = X^1 + X^2 + X^4 + X^5 + X^3$;
$E_1 = X^2 + X^3$;
$F_1 = X^7$; and
$G_1 = 2X^1 + X^6$.

Accordingly, the amounts $X^1$ to $X^7$ of the respective polyamine componnets can be given by solving the above set of the simultaneous equations. The results of the solution giving $X^1$ to $X^7$ as a function of $A_1$ to $G_1$ are as follows.

$X^1 = B_1 - E_1$;
$X^2 = A_1 + 2E_1 - 2B_1$;
$X^3 = 2B_1 - A_1 - E_1$;
$X^4 = C_1 + E_1 - B_1 - D_1$;
$X^5 = 2B_1 + 2D_1 - 2E_1 - A_1 - C_1$;
$X^2 = 2E_1 + G_1 - 2B_1$; and
$X^7 = F_1$.

The amount of hydrogen peroxdie produced in each of the steps $A_1$ to $G_1$ can be determined by any conventional method known in the analytical chemistry including the colorimetric method, fluorescence spectrophotometric method, chemiluminescence method by use of luminal and other suitable methods, among which the most convenient is the colorimetric or spectrophotometric method by use of a coloring agent which may be one of the 4-aminoantipyrine/phenol/peroxidase system or the 4-aminoantipyrine/N,N-diethylaniline/peroxidase system capable of giving coloration with very large molecular extinction coefficients. When such a colorimetric method is used for the determination of the hydrogen peroxide, the above set of the simultaneous equations for $X^1$ to $X^7$ can be modified into a set of simultaneous equations for $x^1$ to $x^7$ each for the molar concentration of one of the polyamine components in the aqueous mixture as a function of the absorbance or increment of the absorbance $a_1$ to $g_1$ in the solutions after the respective steps due to the coloration with the hydrogen peroxide as divided by the molecular extinction coefficient. Alternatively, it is optional that, in place of the direct determination of the hydrogen peroxide, the decrease of the oxygen in the atmosphere above the reaction mixture is determined when the enzymatic reaction is undertaken in a closed system.

Although the above description is given for the principle of the inventive method applied to an aqueous mixture containing all of the 7 polyamine components, for which the number of the steps should be 7 to be equal to the number of the polyamine components, it is readily understood that one or more of the steps $A_1$ to $G_1$ can be omitted when absence of one or more of the polyamine components in the starting aqueous mixture is definitely indicated by a preliminary qualitative assay of the mixture so that the number of the steps of the enzymatic reactions in some cases can be reduced to be equal to the number of the polyamine components to be determined.

For example, the steps $F_1$ and $G_1$ can be omitted when the aqueous mixture contains only spermine, spermidine, putrescine, acetylspermine and $N^1$-acetylspermidine among the 7 polyamine components and the step $F_1$ can be omitted when acetylputrescine is absent. Similarly, the step $G_1$ can be omitted when $N^8$-acetylspermidine is not contained and a combination of the steps $A_1$, $B_1$, $E_1$ and $G_1$ is sufficient for the analysis of an aqueous mixture containing no acetylspermine, $N^1$-acetylspermidine and acetylputrescine. Further, combinations of the steps $A_1$, $B_1$, $E_1$ and $F_1$ and the steps of $A_1$, $B_1$, $E_1$, $F_1$ and $G_1$ are sufficient for the analysis of aqueous mixtures containing no acetylspermine and $N^1$- and $N^8$-acetylspermidines and no acetylspermine and $N^1$-acetylspermidine, respectively.

Following is a description of the second of the preferable embodiments of the inventive method applied to an aqueous mixture containing all of the 7 polyamine components. The analytical procedure comprises following 7 steps $A_2$ to $G_2$.

Step $A_2$:

A volume of the aqueous mixture is admixed with at least 0.1 unit of putrescine oxidase to effect the enzymatic oxidation of the putrescine contained therein at a pH of 7.5–9 or, preferably, 8–8.5 and the amount of the hydrogen peroxide produced by the reaction is determined after completion of the reaction. Assume that the thus determined amount of the hydrogen peroxide is equal to $A_2$ moles, $A_2$ being equal to the summation of the numbers of moles of the spermidine and putrescine contained in the aqueous mixture.

Step $B_2$:

The pH of the aqueous mixture after completion of the step $A_2$ above is adjusted to 5–7 or, preferably, 6–6.5 and about 0.02 to 0.1 unit of polyamine oxidase AT-1 is added thereto to effect the enzymatic oxidation of spermine. The amount of hydrogen peroxide produced by the reaction is determined after completion of the reaction. Assume that the thus determined amount of the hydrogen peroxide is equal to $B_2$ moles, $B_2$ being equal to twice of the number of moles of the spermine contained in the aqueous mixture. Note that 1 mole of putrescine is produced per mole of the spermine.

Step $C_2$:

The aqueous mixture after completion of the step $B_2$ above is further admixed with an additional amount of at least 2 units of polyamine oxidase AT-1 to effect the enzymatic oxidation of the acetylspermine and $N^1$-acetylspermidine and the amount of hydrogen peroxide produced by the reaction is determined after completion of the reaction. Assume that the thus determined amount of the hydrogen peroxide is equal to $C_2$ moles, $C_2$ being equal to the summation of the twice number of moles of the acetylspermine and the number of moles of the $N^1$-acetylspermidine contained in the aqueous mixture. Note that 1 mole of putrescine is produced in this step per mole of each of these acetylated polyamines.

Step $D_2$:

The pH of the mixture after completion of the step $C_2$ above is adjusted again to about 8.5 so that the activity of the putrescine oxidase added in the step $A_2$, which has been inactive at a pH of 5–6.5 in the step $B_2$, is resumed to effect enzymatic oxidation of the amount of putrescine produced from spermine in the step $B_2$ and from acetylspermine and $N^1$-acetylspermidine in the step $C_2$. Assume that the amount of the hydrogen peroxide determined after completion of the reaction is equal to $D_2$ moles, $D_2$ being equal to the summation of the numbers of moles of the above mentioned three kinds of the free and acetylated polyamines.

Step $E_2$:

Another portion of the aqueous mixture containing the 7 kinds of the free and acetylated polyamines is admixed with about 0.1–0.2 unit of polyamine oxidase PC-3 at a pH of about 5–6 to effect the enzymatic oxidation of the spermine and spermidine contained therein and the amount of hydrogen peroxide produced by the reaction is determined after completion of the reaction. Assume that the thus determined amount of hydrogen peroxide is equal to $E_2$ moles, $E_2$ being equal to the summation of the numbers of moles of the spermine and spermidine.

Step $F_2$:

The aqueous mixture after completion of the step $E_2$ above is further admixed with an additional amount of at least 15 units of polyamine oxidase PC-3 to effect enzymatic oxidation of $N^8$-acetylspermidine and the amount of hydrogen peroxide is determined after completion of the reaction. Assume that the thus determined amount of hydrogen peroxide is equal to $F_2$ moles, $F_2$ being equal to the number of moles of the $N^8$-acetylspermidine contained in the aqueous mixture. Note that 1 mole of acetylputrescine is produced in this step per mole of the $N^8$-acetylspermidine.

Step $G_2$:

The pH of the aqueous mixture after completion of the step $F_2$ is adjusted to about 8.0 and 0.05 to 0.5 unit of acetylputrescine oxidase is added thereto to effect enzymatic oxidation of the acetylputrescine. The amount of the substrate decomposed in this step is a summation of the content in the starting aqueous mixture and the amount produced in the preceding step $F_2$. Assume that the amount of the hydrogen peroxide determined after completion of the reaction is equal to $G_2$ moles, $G_2$ being equal to the summation of the numbers of moles of the acetylputrescine and $N^8$-acetylspermidine contained in the starting aqueous mixture.

When the amounts of the hydrogen peroxide $A_2$ to $G_2$ in the respective steps have been obtained, following set of simultaneous equations can be set up each giving one of the values $A_2$ to $G_2$ as a function of the respective contents $X^1$ to $X^7$ of the 7 kinds of the free and acetylated polyamines as defined before:

| | |
|---|---|
| $A_2 = X^2 + X^3$; | $E_2 = 2X^1 + X^2$; |
| $B_2 = 2X^1$; | $F_2 = X^6$; and |
| $C_2 = 2X^4 + X^5$; | $G_2 = X^7 + X^6$. |
| $D_2 = X^1 + X^4 + X^5$; | |

By solving the above given set of the simultaneous equations in terms of the contents $X^1$ to $X^7$ of the polyamines, each of $X^1$ to $X^7$ can be given as a function of the known amounts of hydrogen peroxide $A_2$ to $G_2$ as follows:

| | |
|---|---|
| $X^1 = \tfrac{1}{2}B_2$; | $X^5 = 2D_2 - B_2 - C_2$; |
| $X^2 = E_2 - B_2$; | $X^6 = F_2$; and |

-continued $X^3 = A_2 + B_2 - E_2;$    $X^7 = G_2 - F_2.$
$X^4 = \frac{1}{2}B_2 + C_2 - D_2;$ When the determination of the hydrogen peroxide is performed colorimetrically to give an increment of the absorbance of the mixture $a_2$ to $g_2$ in each of the steps $A_2$ to $G_2$, the molar concentration $x^1$ to $x^7$ of each of the polyamine components in the aqueous mixture can be given by one of the simultaneous equations obtained by the modification of the above set of equations in a similar manner to the first embodiment by dividing the values of $a_2$ to $g_2$ by the molar extinction coefficient in place of $A_2$ to $G_2$ in the equations for $X^1$ to $X^7$.

It should be understood that, although the above description gives only two of the preferred embodiments of the inventive method, several other procedures are possible with different sequences and combinations of the enzymatic reactions to give a set of simultaneous equations with the contents or concentrations of the polyamine components as the unknowns by use of the enzymes. Further, the principle of the inventive method is applicable to a combination of other enzymes with modified sequence of the reactions provided that the substrate specificity thereof is similar to, though not necessarily the same as, the 4 enzymes utilized here.

In accordance with the above described method of the present invention, a great advantage is obtained in the diagnosis of and estimation of the therapeutic effect on the patients suffering cancer or other diseases with the contents of individual free and acetylated polyamines in the body fluids as a clue, which can be determined very rapidly and conveniently with reliableness in contrast to the conventional chemical methods which can be performed only with extreme difficulties even by use of an expensive instrument such as a high-speed liquid chromatograph, amino acid analyzer and the like.

Following is a further description of the inventive method by way of Examples with several living body samples preceded by several standardizing experiments each with known amounts of one or two of the polyamines in question.

In the Standardizing Experiments and Examples given below, each of the acetylated polyamines was synthesized from the corresponding free polyamine according to the procedure described in Methods in Enzymology, volume 17 B, pages 829-833.

Standardizing Experiment 1

A coloring solution was prepared by dissolving 5 mg of peroxidase (product by Boehringer Mannheim GmbH, grade II), 0.2 ml of phenol and 10 mg of 4-aminoantipyrine in 100 ml of a 0.1M phosphate buffer solution having a pH of 6.5.

The enzymatic oxidative decomposition reaction of spermine as the substrate was performed in an aqueous mixture prepared by mixing 1.5 ml of the above prepared coloring solution, 0.5 ml of a commercially available 400 μM aqueous solution of spermine and 0.49 ml of distilled water with admixture of, after a preheating for 3 minutes at 35° C., 10 μl of polyamine oxidase AT-1 corresponding to 0.05 unit. This aqueous solution was subjected to the colorimetric determination of the hydrogen peroxide produced by the reaction with a reference of an aqueous solution prepared in the same manner as above except that the substrate solution was replaced with the same volume of distilled water.

Figure 1:
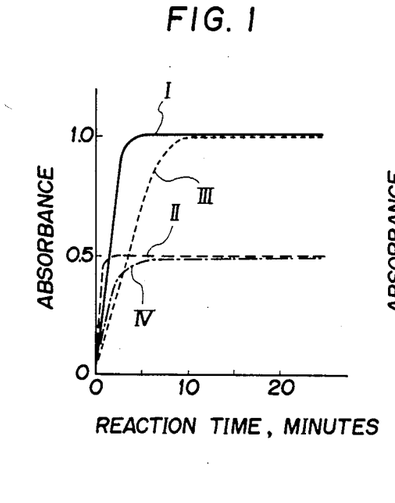
FIG. 1 illustrates the graphs showing the increase of the absorbance in time in the photometric solutions. See Standardizing Experiments 1, 2, 3 and 4 in the text for the curves I, II, III and IV, respectively.

The increase in the absorbance of the solution at a wavelength of 505 nm was followed for 20 minutes after the addition of the enzyme and the results are shown in FIG. 1 with the full line marked I. As is clear from this figure, the absorbance levelled off already 5 minutes after the start of the reaction reaching a value of 1.00 when the reaction was taken as complete. The above value of the absorbance corresponds to the formation of 2 moles of hydrogen peroxide per mole of spermine.

Figure 2:
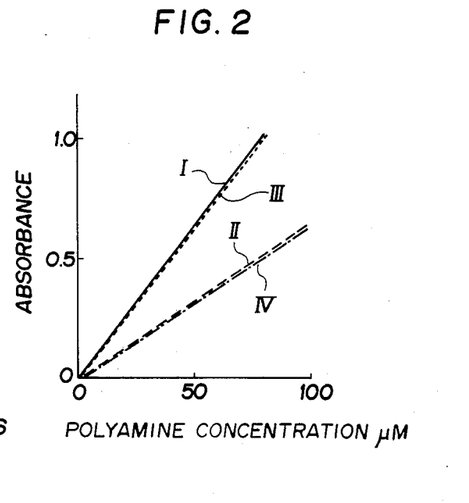
FIG. 2 illustrates the graphs showing the linear relationship between the concentration of polyamines and the maximum absorbance of the photometric solution. See Standardizing Experiments 1, 2, 3 and 4 in the text for the curves I, II, III and IV, respectively.

The same experiment as above was repeated several times except that the concentration of the substrate solution was varied in the range from 10 to 100 μM and the results of the maximum absorbances obtained in these experiments are plotted in FIG. 2 to give the full line marked I taking the concentration of the substrate solution as the abscissa and the maximum absorbance as the ordinate. As is clear from this figure, good linearity was obtained in the relationship between the concentration of the substrate and the absorbance indicating the reliability of this method for the analytical purpose.

Standardizing Experiment 2

The same experimental procedure as in Standardizing Experiment 1 above was repeated except that the substrate was a commercially available product of spermidine in place of spermine. The results are shown similarly in FIGS. 1 and 2 each with the broken line marked II. As is clear from FIG. 1, the reaction was complete within 5 minutes and 1 mole of hydrogen peroxide was produced per mole of the substrate. The linearity was also good in the relationship between the substrate concentration and the maximum absorbance as is shown in FIG. 2.

Standardizing Experiment 3

The same experimental procedure as in Standardizing Experiment 1 above was repeated except that the substrate was acetylspermine in place of spermine and the amount of the enzyme was increased to 2 units. The results are shown similarly in FIGS. 1 and 2 each with the dotted line marked III. As is clear from FIG. 1, the reaction was complete within 10 minutes and 2 moles of hydrogen peroxide were produced per mole of the substrate. The linearity was also good in the relationship between the substrate concentration and the maximum absorbance as is shown in FIG. 2.

Standardizing Experiment 4

The same experimental procedure as in Standardizing Experiment 1 above was repeated except that the substrate was $N^1$-acetylspermidine in place of spermine. The results are shown similarly in FIGS. 1 and 2 each with the chain line marked IV. As is clear from FIG. 1, the reaction was complete within about 10 minutes and 1 mole of hydrogen peroxide was produced per mole of the substrate. The linearity was also good in the relationship between the substrate concentration and the maximum absorbance as is shown in FIG. 2.

Standardizing Experiment 5

The same experimental procedure as in Standardizing Experiment 1 above was repeated except that the coloring solution was prepared by use of a 0.1M phosphate buffer solution having a pH of 5.5 in place of 6.5 and about 0.05 unit of polyamine oxidase PC-3 was used in place of the polyamine oxidase AT-1. The results of the measurements of the absorbance as plotted in graphs similar to FIGS. 1 and 2 indicated that the reaction was complete within about 5 minutes and 2 moles of hydrogen peroxide were produced per mole of the substrate. The linearity was also good in the relationship between the substrate concentration and the maximum absorbance.

Standardizing Experiment 6

The same experimental procedure as in Standardizing Experiment 5 above was repeated except that the substrate was spermidine in place of the spermine. The results of the measurements of the absorbance as plotted in graphs similar to FIGS. 1 and 2 indicated that the reaction was complete within about 10 minutes and 1 mole of hydrogen peroxide was produced per mole of the substrate. The linearity was also good in the relationship between the substrate concentration and the maximum absorbance.

Standardizing Experiment 7

The same experimental procedure as in Standardizing Experiment 5 above was repeated except that the substrate was $N^8$-acetylspermidine in place of the spermine and the amount of the enzyme was increased to about 15 units. The results of the measurements of the absorbance as plotted in graphs similar to FIGS. 1 and 2 indicated that the reaction was complete within about 10 minutes and 1 mole of hydrogen peroxide was produced per mole of the substrate. The linearity was also good in the relationship between the substrate concentration and the maximum absorbance.

Standardizing Experiment 8

The same experimental procedure as in Standardizing Experiment 1 above was repeated except that the coloring solution was prepared by use of a 0.1M borate buffer solution having a pH of 8.5 in place of the phosphate buffer solution and the substrate and the enzyme were a commercially available product of putrescine and putrescine oxidase in an amount of about 0.5 unit, respectively, in place of the spermine or polyamine oxidase AT-1. The results of the measurements of the absorbance as plotted in graphs similar to FIGS. 1 and 2 indicated that the reaction was complete within about 5 minutes and 1 mole of hydrogen peroxide was produced per mole of the substrate. The linearity was also good in the relationship between the substrate concentration and the maximum absorbance.

Standardizing Experiment 9

The same experimental procedure as in Standardizing Experiment 8 above was repeated except that the substrate was a commercially available product of spermidine in place of putrescine. The results of the measurements of the absorbance as plotted in graphs similar to FIGS. 1 and 2 indicated that the reaction was complete within 10 minutes and 1 mole of hydrogen peroxide was produced per mole of the substrate. The linearity was also good in the relationship between the substrate concentration and the maximum absorbance.

Standardizing Experiment 10

The same experimental procedure as in Standardizing Experiment 1 above was repeated except that the coloring solution was prepared by use of a 0.1M phosphate buffer solution having a pH of 8.0 in place of 6.5 and the substrate and the enzyme were acetylputrescine and acetylputrescine oxidase in an amount of about 0.5 unit, respectively, in place of the spermine or polyamine oxidase AT-1. The results of the measurements of the absorbance as plotted in graphs similar to FIGS. 1 and 2 indicated that the reaction was complete within about 5 minutes and 1 mole of hydrogen peroxide was produced per mole of the substrate. The linearity was also good in the relationship between the substrate concentration and the maximum absorbance.

Standardizing Experiment 11

The enzymatic oxidative decomposition reaction of spermine as the substrate was undertaken in an aqueous mixture prepared by mixing 1.5 ml of the coloring solution prepared in Standardizing Experiment 1 above, 0.5 ml of a 400 $\mu$M aqueous solution of spermine and 0.19 ml of distilled water with admixture of, after a preheating for 3 minutes at 35° C., 10 $\mu$l of polyamine oxidase AT-1 corresponding to an amount of 0.05 unit. After about 5 minutes to effect the reaction, the aqueous mixture was further admixed with about 0.3 ml of a 0.3M aqueous solution of sodium borate so that the pH of the mixture was brought to 8-9 with the total volume of the mixture increased to 2.5 ml. The absorbance of this mixture at a wavelength of 505 nm was 1.00. The above procedure is called the first step.

Thereafter, the aqueous mixture after the first step was further admixed with 5 $\mu$l of putrescine oxidase corresponding to an amount of 0.5 unit and the absorbance of the mixture at the same wavelength as above was measured after 5 minutes of the reaction to give a value of 1.50 with an increment of 0.50 after the addition of the putrescine oxidase. This procedure following the first step is called the second step.

Figure 3:
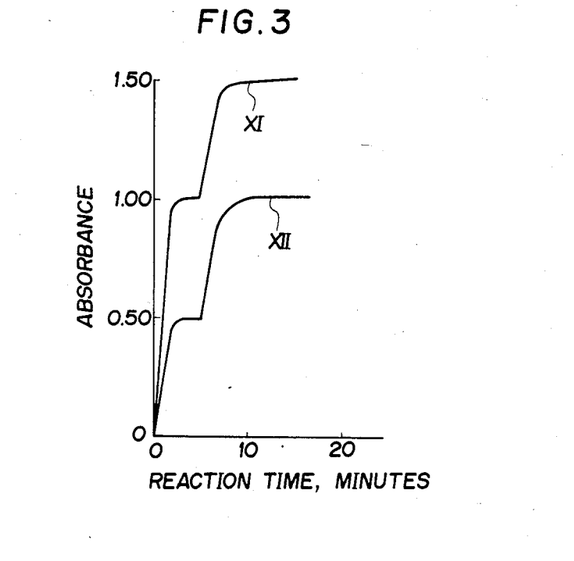
FIG. 3 illustrates the graphs showing the two-step increase of the absorbance in time in the photometric solutions. See Standardizing Experiments 11 and 12 in the text for the curves XI and XII, respectively.

The results of the measurements of the absorbance are shown in FIG. 3 with the curve marked XI as a function of time. As is shown in this figure, the two-step curve XI has two plateaus at absorbances of 1.00 and 1.50 corresponding to the completion of the reactions in the first and second steps, respectively. This result indicates that 2 moles and 1 mole of hydrogen peroxide are produced per mole of spermine in the first step and per mole of putrescine in the second step, respectively, the putrescine having been produced in the first step.

Standardizing Experiment 12

The same experimental procedure as in Standardizing Experiment 11 above was repeated except that the substrate was spermidine in place of spermine. The results of the measurements of the absorbance are shown by the two-step curve XII in FIG. 3 having two plateaus at absorbances of 0.50 and 1.00 with an increment of 0.50 in the second step indicating that 1 mole of hydrogen peroxide was produced per mole of the spermidine in the first step and 1 mole of hydrogen peroxide was produced in the second step per mole of putrescine, the putrescine having been produced in the first step.

Standardizing Experiment 13

The same experimental procedure as in Standardizing Experiment 11 above was repeated except that 0.5 ml of a 400 $\mu$M solution of acetylspermine was used as the substrate in place of the spermine and the amount of the enzyme polyamine oxidase AT-1 was increased to about 5 units (the liquid volume was also 10 $\mu$l). The results of the measurements of the absorbance as plotted in a graph similar to FIG. 3 gave a two-step curve similar to the curve XI in FIG. 3 having two plateaus at absorbances of 1.00 and 1.50 with an increment of 0.50 in the second step indicating that 2 moles and 1 moles of hydrogen peroxide were produced per mole of the acetylspermine in the first and second steps, respectively.

Standardizing Experiment 14

The same experimental procedure as in Standardizing Experiment 13 was repeated except that the substrate was $N^1$-acetylspermidine added as a 400 μM solution in a volume of 0.5 ml. The results of the measurements of the absorbance as plotted in a graph similar to FIG. 3 gave a two-step curve similar to the curve XII having two plateaus at absorbances of 0.50 and 1.00 with an increment of 0.50 in the second step indicating that 1 mole of hydrogen peroxide was produced in each of the first and second steps per mole of the $N^1$-acetylspermidine.

Standardizing Experiment 15

The enzymatic oxidative decomposition reaction of spermine as the substrate was undertaken in an aqueous mixture prepared by mixing 1.5 ml of a coloring solution prepared in the same manner as in Standardizing Experiment 1 but by use of a 0.1M acetate buffer solution having a pH of 5.0, 0.5 ml of a 400 μM solution of spermine and 0.19 ml of distilled water with admixture of, after a preheating for 3 minutes at 35° C., 10 μl of polyamine oxidase PC-3 corresponding to an amount of about 0.05 unit. After about 5 minutes to complete the reaction, the aqueous mixture was further admixed with a 0.3M aqueous solution of sodium borate so that the pH of the mixture was brought to 8-8.5 and the total volume of the mixture was 2.5 ml and the absorbance of the mixture at a wavelength of 505 nm was measured to give a value of 1.00. The above procedure is called the first step.

The aqueous solution after completion of the first step was further admixed with 5 μl of putrescine oxidase corresponding to an amount of about 0.5 unit and a further enzymatic reaction was performed for 5 minutes and the absorbance of the mixture was measured at the same wavelength to give a value of 1.50 with an increment of 0.50 in this procedure following the first step, which is called the second step.

The results of the measurements of the absorbance as plotted in a graph similar to FIG. 3 as a function of time gave a two-step curve similar to the curve XI in FIG. 3 having two plateaus at absorbances of 1.00 and 1.50 indicating that 2 moles and 1 mole of hydrogen peroxide were produced in the first and second steps, respectively, per mole of the spermine.

Standardizing Experiment 16

The same experimental procedure as in Standardizing Experiment 15 was repeated except that the substrate was spermidine added as a 100 μM solution in a volume of 0.5 ml. The results of the measurements of the absorbance as plotted in a graph similar to FIG. 3 gave a two-step curve similar to the curve XII in FIG. 3 having two plateaus at absorbances of 0.50 and 1.00 with an increment of 0.50 in the second step indicating that 1 mole of hydrogen peroxide was produced per mole of the spermidine in each of the first and second steps.

Standardizing Experiment 17

The enzymatic oxidative decomposition reaction of $N^8$-acetylspermidine as the substrate was performed in an aqueous mixture prepared by mixing 1.5 ml of the same coloring solution as in Standardizing Experiment 5, 0.5 ml of a 400 μM solution of $N^8$-acetylspermidine and 0.44 ml of distilled water with admixture of, after a preheating for 3 minutes at 35° C., 10 μl of polyamine oxidase PC-3 corresponding to an amount of about 15 units to start the reaction. The reaction was complete within about 10 minutes. Thereafter, the aqueous mixture was further admixed with 50 μl of a 5N aqueous solution of sodium hydroxide so that the pH of the mixture was brought to about 7.5 with the total volume of the mixture of 2.5 ml and the absorbance of the mixture was measured at a wavelength of 505 nm to give a value of 0.500. The above procedure is called the first step.

In the next place, the aqueous mixture after completion of the first step was further admixed with 5 μl of acetylputrescine oxidase corresponding to an amount of about 0.5 unit to effect a further enzymatic reaction for about 10 minutes and the absorbance of the mixture was measured to give a value of 1.000 with an increment of 0.500 after the first step. This procedure following the first step is called the second step.

The results of the measurements of the absorbance as plotted in a graph similar to FIG. 3 gave a two-step curve similar to the curve XII in FIG. 3 having two plateaus at absorbances of 0.500 and 1.000 with an increment of 0.500 in the second step indicating that 1 mole of hydrogen peroxide was produced per mole of the $N^8$-acetylspermidine in each of the first and second steps.

EXAMPLE 1

Into a photometric cell of 3 ml capacity was introduced an aqueous mixture prepared by mixing 1.5 ml of the same coloring solution as in Standardizing Experiment 1, 7 aqueous solutions each in a volume of 25 μl containing either one of the 7 polyamines, i.e. spermine, spermidine, putrescine, acetylspermine, $N^1$- and $N^8$-acetylspermidines and acetylputrescine, in a concentration of 2.0 mM and 0.52 ml of distilled water. The concentration of each of the polyamines was about 20 μM in this aqueous mixture after the addition of the undermentioned sodium borate solution.

After a preheating for 3 minutes at 35° C., the aqueous mixture in the cell was further admixed with 5 μl of polyamine oxidase AT-1 corresponding to an amount of about 0.1 unit and the enzymatic reaction was performed for about 5 minutes followed by the addition of 0.3 ml of a 0.3M aqueous solution of sodium borate to bring the pH of the mixture to 8-8.5 and measurement of the absorbance at a wavelength of 505 nm. This procedure corresponds to the step $A_1$ in the first embodiment of the inventive method described before.

The aqueous mixture after the step $A_1$ was admixed with 5 μl of putrescine oxidase corresponding to an amount of about 5 units and the enzymatic reaction was performed at 35° C. for 15 minutes followed by the measurement of the absorbance. This step corresponds to the step $B_1$ in the first embodiment of the inventive method described before.

Separately, the same volume of the aqueous mixture containing 7 kinds of the polyamines as above before the addition of polyamine oxidase AT-1 in the step $A_1$ was admixed with, after a preheating for 3 minutes at 35° C., 15 μl of polyamine oxidase AT-1 corresponding to an amount of about 3 units and the enzymatic reaction was performed for 10 minutes. The mixture after completion of the reaction was admixed with 0.3 ml of a 0.3M aqueous solution of sodium borate followed by the measurement of the absorbance at a wavelength of 505 nm. This step corresponds to the step $C_1$ in the first embodiment of the inventive method described before.

The aqueous mixture after the step $C_1$ was admixed with 5 µl of putrescine oxidase corresponding to an amount of about 5 units and the enzymatic reaction was performed at 35° C. for 15 minutes followed by the measurement of the absorbance. This step corresponds to the step $D_1$ in the first embodiment of the inventive method described before.

Further separately, another volume of an aqueous mixture was prepared by mixing 0.52 ml of distilled water, 7 aqueous solutions each in a volume of 25 µl containing either one of the 7 polyamines in a concentration of 2.0 mM and 1.5 ml of a coloring solution prepared in the same manner as in Standardizing Experiment 1 but by use of a buffer solution which was a 1:1 by volume mixture of a 0.1M phosphate buffer solution having a pH of 8.5 and a 0.1M sodium carbonate/potassium chloride/boric acid buffer solution having a pH of 8.5. After a preheating at 35° C. for 3 minutes, the above prepared aqueous mixture was admixed with 10 µl of putrescine oxidase corresponding to an amount of about 5 units and the enzymatic reaction was performed for about 15 minutes followed by the addition of 20 µl of a 5N hydrochloric acid and measurement of the absorbance at a wavelength of 505 nm. This step corresponds to the step $E_1$ in the first embodiment of the inventive method described before.

The aqueous mixture after completion of the step $E_1$ was admixed with 5 µl of acetylputrescine oxidase corresponding to an amount of about 0.5 unit and the enzymatic reaction was performed for 10 minutes followed by the measurement of the absorbance at a wavelength of 505 nm. This step corresponds to the step $F_1$ in the first embodiment of the inventive method described before.

The aqueous mixture after completion of the step $F_1$ was admixed with 20 µl of a 5N hydrochloric acid so that the pH of the mixture was 5-5.5 and further with about 5 µl of polyamine oxidase PC-3 corresponding to an amount of about 15 units to effect the enzymatic reaction for about 15 minutes followed by the measurement of the absorbance at a wavelength of 505 nm. This procedure corresponds to the step $G_1$ in the first embodiment of the inventive method described before.

The values $a_1$, $b_1$, $c_1$, $d_1$, $e_1$, $f_1$ and $g_1$ of the adsorbance or increment of the adsorbance in the steps $A_1$ to $G_1$ above were 0.375, 0.375, 0.750, 0.497, 0.250, 0.123 and 0.370, respectively. The values of the molar concentrations of the 7 polyamines in the photometric solutions $x^1$ to $x^7$, which should be each 20.0 µM as calculated, could be determined by solving the set of simultaneous equations obtained by the substitution of the values of $a_1$ to $g_1$ as divided by the molecular extinction coefficient 6250 for $A_1$ to $G_1$, respectively, and $x^1$ to $x^7$ for $X^1$ to $X^7$, respectively, in the simultaneous equations giving $X^1$ to $X^7$ as functions of $A_1$ to $G_1$. The results are as follows:

| | |
|---|---|
| $x^1$ for spermine | 20.0 µM; |
| $x^2$ for spermidine | 20.0 µM; |
| $x^3$ for putrescine | 20.0 µM; |
| $x^4$ for acetylspermine | 20.5 µM; |
| $x^5$ for $N^1$—acetylspermidine | 19.0 µM; |
| $x^6$ for $N^8$—acetylspermidine | 19.2 µM; and |
| $x^7$ for acetylputrescine | 19.7 µM. |

The above results support the surprisingly good reliability of the inventive method with an extremely small deviation of the found value of the concentration of each of the polyamines from the calculated concentration of 20 µM of the respective polyamine contained in the photometric solution.

EXAMPLE 2

Into a photometric cell of 3 ml capacity were introduced 1.5 ml of a coloring solution prepared by dissolving 5.0 mg of peroxidase (a product by Boehringer Mannheim GmbH, Grade II), 10.0 mg of 4-aminoantipyrine and 54.8 mg of sodium N-ethyl-N-(2-hydroxy-3-sulfopropyl) m-toluidine in 100 ml of a 1:1 by volume mixture of a 0.1M phosphate buffer solution having a pH of 8.5 and a 0.1M sodium carbonate/potassium chloride/boric acid buffer solution having a pH of 8.5, 0.5 ml of human urine and 0.46 ml of distilled water with admixture of, after a preheating for 3 minutes at 35° C., 5 µl of putrescine oxidase corresponding to an amount of about 5 units and the enzymatic reaction was performed for about 15 minutes. After completion of the reaction, 30 µl of a 5N hydrochloric acid were added to the photometric cell so that the pH of the aqueous mixture was 6-6.5 followed by the measurement of the absorbance at a wavelength of 555 nm. The above procedure corresponds to the step $A_2$ in the second embodiment of the inventive method described before.

The aqueous mixture after the step $A_2$ above was admixed with 5 µl of polyamine oxidase AT-1 corresponding to an amount of about 0.1 unit and the absorbance of the mixture was measured at the same wavelength after 5 minutes of the reaction time. This procedure following the step $A_2$ above corresponds to the step $B_2$ in the second embodiment of the inventive method described before.

The aqueous mixture after the step $B_2$ above was further admixed with 5 µl of polyamine oxidase AT-1 corresponding to an amount of about 5 units and the absorbance of the mixture was measured at the same wavelength after 10 minutes of the reaction time. This procedure following the step $B_2$ above corresponds to the step $C_2$ in the second embodiment of the inventive method described before.

The aqueous mixture after the step $C_2$ above was admixed with 30 µl of a 5N aqueous solution of sodium hydroxide so that the pH of the mixture was again about 8.5 to reactivate the putrescine oxidase added in the step $A_2$ and the absorbance of the mixture was measured at the same wavelength after 15 minutes of the reaction at 35° C. This procedure following the step $C_2$ above corresponds to the step $D_2$ in the second embodiment of the inventive method described before.

Separately, into another photometric cell of 3 ml capacity were introduced 1.5 ml of a coloring solution prepared in the same manner as in the step $A_2$ but by use of a 0.1M phosphate buffer solution having a pH of 5.5, 0.5 ml of the same human urine and 0.49 ml of distilled water with admixture of, after a preheating at 35° C. for 3 minutes, 5 µl of polyamine oxidase PC-3 corresponding to an amount of about 0.1 unit and the absorbance of the mixture was measured at a wavelength of 555 nm after 5 minutes of the reaction time. This procedure corresponds to the step $E_2$ in the second embodiment of the inventive method described before.

The aqueous mixture after the step $E_2$ was further admixed with 5 µl of polyamine oxidase PC-3 corresponding to an amount of about 15 units and the absorbance of the mixture was measured at the same wavelength after about 15 minutes of the reaction time. This procedure following the step $E_2$ above corresponds to the step $F_2$ in the second embodiment of the inventive method described before.

The aqueous mixture after the step $F_2$ above was further admixed with 45 μl of a 5N aqueous solution of sodium hydroxide to bring the pH of the mixture to about 7.5 and then with 5 μl of acetylputrescine oxidase corresponding to an amount of about 0.5 unit and the absorbance of the mixture was measured at the same wavelength after 15 minutes of the reaction time. This procedure following the step $F_2$ above corresponds to the step $G_2$ in the second embodiment of the inventive method described before.

The values of the absorbance or increment of the absorbance $a_2$, $b_2$, $c_2$, $d_2$, $e_2$, $f_2$ and $g_2$ obtained in the above steps $A_2$ to $G_2$ were 0.024, 0.018, 0.011, 0.020, 0.028, 0.005 and 0.035, respectively. The values of the molar concentrations $x^1$ to $x^7$ of the 7 polyamines in the photometric solutions could be determined by solving the set of simultaneous equations obtained by the substitution of the values of $a_2$ to $g_2$ as divided by the molecular extinction coefficient of 17,200 for $A_2$ to $G_2$, respectively, and $x^1$ to $x^7$ for $X^1$ to $X^7$, respectively, in the simultaneous equations giving $X^1$ to $X^7$ as functions of $A_2$ to $G_2$ and the concentrations of the polyamines in the urine were calculated from the values of $x^1$ to $x^7$. The results were as tabulated below.

| Polyamine | Concentration in the photometric solution, μM | Concentration in the urine, μM |
|---|---|---|
| Spermine | $x^1 = 0.52$ | 2.6 |
| Spermidine | $x^2 = 0.58$ | 2.9 |
| Putrescine | $x^3 = 0.81$ | 4.1 |
| Acetylspermine | $x^4 = 0.00$ | 0 |
| $N^1$—Acetylspermidine | $x^5 = 0.64$ | 3.2 |
| $N^8$—Acetylspermidine | $x^6 = 0.29$ | 1.5 |
| Acetylputrescine | $x^7 = 1.74$ | 8.7 |

EXAMPLE 3

Red blood corpuscles in a volume of 2.5 ml were suspended in 6.5 ml of distilled water with vigorous agitation for 1 minute and the suspension was admixed with 1 ml of a 30% aqueous solution of perchloric acid and vigorously agitated for 2 minutes. The insoluble precipitates were removed by centrifugal separation at a velocity of 3000 r.p.m. for 10 minutes and the clear solution was admixed with a 7.5M aqueous solution of sodium carbonate to have a pH of about 7. The thus obtained solution was used as a test solution for the determination of polyamines.

A coloring solution was prepared with the same formulation as in Example 2 excepting the use of a 0.1M phosphate buffer solution having a pH of 6.5 in place of the buffer solution having a pH of 8.5 or 5.5. Into a photometric cell of 3 ml capacity were taken 1.5 ml of the above coloring solution, 0.5 ml of the test solution and 0.195 ml of distilled water followed, after a preheating for 3 minutes at 35° C., by the admixture of 5 μl of polyamine oxidase AT-1 corresponding to an amount of about 0.1 unit to effect the enzymatic reaction for about 5 minutes. After completion of the reaction, the aqueous mixture was further admixed with 0.3 ml of a 0.3M sodium borate solution to have a pH of 8 to 8.5 and the absorbance of the mixture was measured at a wavelength of 555 nm. The above procedure corresponds to the step $A_1$ of the first embodiment of the inventive method described before.

The aqueous solution having a pH of 8-8.5 after completion of the above step $A_1$ was admixed with 5 μl of putrescine oxidase corresponding to an amount of about 5 units and the absorbance at a wavelength of 555 nm was measured after about 15 minutes of the reaction at 35° C. This step following the step $A_1$ above corresponds to the step $B_1$ in the first embodiment of the inventive method described before.

Separately, another 0.5 ml portion of the test solution prepared from the red blood corpuscles was admixed with 0.195 ml of distilled water and 1.5 ml of the same coloring solution as used in the step $A_1$ above followed, after a preheating for 3 minutes at 35° C., by the addition of 5 μl of polyamine oxidase AT-1 corresponding to an amount of about 3 units to effect the enzymatic reaction for 10 minutes. The aqueous mixture after completion of the above reaction was admixed with 0.3 ml of a 0.3M aqueous solution of sodium borate and the absorbance of the mixture was measured at a wavelength of 555 nm. This procedure corresponds to the step $C_1$ in the first embodiment of the inventive method described before.

The aqueous mixture after completion of the step $C_1$ above was further admixed with 5 μl of putrescine oxidase corresponding to an amount of about 5 units and the absorbance of the mixture was measured at a wavelength of 555 nm after 15 minutes of the reaction. This procedure following the above mentioned step $C_1$ corresponds to the step $D_1$ in the first embodiment of the inventive method described before.

Another coloring solution was prepared with the same formulation as in the step $A_1$ above excepting the use of a buffer solution which was a 1:1 by volume mixture of a 0.1M phosphate buffer solution having a pH of 8.5 and a 0.1M sodium carbonate/ potassium chloride/boric acid buffer solution having a pH of 8.5. Another 0.5 ml portion of the test solution prepared from the red blood corpuscles was admixed with 1.5 ml of the above prepared coloring solution and 0.18 ml of distilled water followed, after a preheating for 3 minutes at 35° C., by the addition of 10 μl of putrescine oxidase corresponding to an amount of about 5 units to effect the enzymatic reaction for about 15 minutes and the absorbance of the aqueous mixture at a wavelength of 555 nm was measured after control of the pH at about 7.5 by the addition of 20 μl of a 6N hydrochloric acid. This procedure following the step $D_1$ above corresponds to the step $E_1$ in the first embodiment of the inventive method described before.

The aqueous mixture after completion of the step $E_1$ above was further admixed with 5 μl of acetylputrescine oxidase corresponding to an amount of about 0.5 unit and the absorbance of the mixture was measured at a wavelength of 555 nm after about 10 minutes of the reaction time. This procedure following the step $E_1$ above corresponds to the step $F_1$ in the first embodiment of the inventive method described before.

The aqueous mixture after completion of the step $F_1$ was admixed with 20 μl of a 5N hydrochloric acid to have a pH of about 5.5 and then with about 5 μl of polyamine oxidase PC-3 corresponding to an amount of about 15 units to effect the enzymatic reaction. The absorbance of the aqueous mixture was measured at a wavelength of 555 nm after about 15 minutes of the reaction time. This procedure following the step $F_1$ above corresponds to the step $G_1$ in the first embodiment of the inventive method described before.

The values of the absorbance or increment of the absorbance $a_1$, $b_1$, $c_1$, $d_1$, $e_1$, $f_1$ and $g_1$ obtained in the above described steps $A_1$ to $G_1$ were 0.034, 0.929, 0.950, 0.040, 0.023, 0.000 and 0.014, respectively, and the calculation to solve the simultaneous equations in a similar manner to the preceding examples with a value of the molecular extinction coefficient of 17,200 gave the values of the molar concentrations $x^1$ to $x^7$ for the 7 polyamines, respectively, in the photometric solutions. These values of $x^1$ to $x^7$ were converted to the molar content of the respective polyamines in the red blood corpuscles. The results were as tabulated below.

| Polyamine | Concentration in the photometric solution, $\mu M$ | Concentration in red blood corpuscles, $\mu M$ |
| --- | --- | --- |
| Spermine | $x^1 = 0.35$ | 7.0 |
| Spermidine | $x^2 = 1.28$ | 25.6 |
| Putrescine | $x^3 = 0.06$ | 1.2 |
| Acetylspermine | $x^4 = 0.23$ | 4.6 |
| $N^1$—Acetylspermidine | $x^5 = 0.47$ | 9.3 |
| $N^8$—Acetylspermidine | $x^6 = 0.12$ | 2.3 |
| Acetylputrescine | $x^7 = 0$ | 0 |

EXAMPLE 4

A coloring solution was prepared with the same formulation as in the Standardizing Experiment 1 excepting the use of a buffer solution which was a 1:1 by volume mixture of a 0.1M phosphate buffer solution having a pH of 8.5 and 0.1M sodium carbonate/potassium chloride/boric acid buffer solution having a pH of 8.5. An aqueous mixture was prepared by mixing 1.5 ml of the above prepared coloring solution, each 50 $\mu l$ of 6 aqueous solutions containing one of the polyamines spermine, spermidine, putrescine, $N^1$- and $N^8$-acetylspermidines and acetylputrescine in a concentration of 2.0 mM, 0.43 ml of distilled water and 0.25 ml of a control plasma solution (Conecella "Nissui") and the aqueous mixture was taken in a 3 ml photometric cell. The concentration of each of the polyamines in this aqueous mixture was 40 $\mu M$. After a preheating for 3 minutes at 35° C., 10 $\mu l$ of putrescine oxidase corresponding to an amount of about 5 units were added to the aqueous mixture to effect the enzymatic reaction for 15 minutes at 35° C. and the absorbance of the aqueous mixture was measured at a wavelength of 505 nm after control of the pH to about 7.5 by the addition of 20 $\mu l$ of a 5N hydrochloric acid. The above procedure is called the step $A_3$.

The aqueous mixture after completion of the step $A_3$ above was admixed with 5 $\mu l$ of acetylputrescine oxidase corresponding to an amount of about 0.5 unit and, after 10 minutes of the reaction time, the absorbance of the aqueous mixture was measured at a wavelength of 505 nm. This procedure following the step $A_3$ above is called the step $B_3$.

The aqueous mixture after completion of the step $B_3$ above was further admixed with 10 $\mu l$ of a 5N hydrochloric acid to have a pH of 6 to 6.5 and then with 5 $\mu l$ of polyamine oxidase AT-1 corresponding to an amount of about 0.1 unit followed by the measurement of the absorbance at a wavelength of 505 nm after 10 minutes of the reaction time. This procedure following the step $B_3$ is called the step $C_3$.

The aqueous mixture after completion of the step $C_3$ above was further admixed with 5 $\mu l$ of polyamine oxidase AT-1 corresponding to an amount of about 5 units and the absorbance of the aqueous mixture was measured at a wavelength of 505 nm after 10 minutes of the reaction time. This procedure following the step $C_3$ is called the step $D_3$.

Separately, another aqueous mixture prepared by mixing each 50 $\mu l$ of the 6 polyamine solutions each containing one of the above mentioned 6 polyamines, 0.25 ml of the control plasma solution, 0.44 ml of distilled water and 1.5 ml of the same coloring solution as used in the Standardizing Experiment 1 was taken in a 3 ml capacity photometric cell followed, after a preheating for 3 minutes at 35° C., by the addition of 5 $\mu l$ of polyamine oxidase PC-3 corresponding to an amount of about 0.1 unit to effect the enzymatic reaction. The absorbance of the aqueous mixture was measured at a wavelength of 505 nm after about 5 minutes of the reaction time at 35° C. This procedure is called the step $E_3$.

The aqueous mixture after completion of the above step $E_3$ was further admixed with 5 $\mu l$ of polyamine oxidase PC-3 corresponding to an amount of about 15 units and the absorbance thereof was measured at a wavelength of 505 nm after about 10 minutes of the reaction time. This procedure following the step $E_3$ is called the step $F_3$.

The values of the absorbance or increment of the absorbance $a_3$, $b_3$, $c_3$, $d_3$, $e_3$ and $f_3$ obtained in the above described steps $A_3$ to $F_3$ were 0.493, 0.245, 0.500, 0.500, 0.746 and 0.242, respectively.

In the above described steps $A_3$ to $F_3$, the molar amounts of the polyamines $X^1$, $X^2$, $X^3$, $X^5$, $X^6$ and $X^7$ for spermine, spermidine, putrescine, $N^1$- and $N^8$-acetylspermidines and acetylputrescine, respectively, and the molar amounts of the hydrogen peroxide $A_3$ to $F_3$ formed in one of the aqueous mixtures in the steps $A_3$ to $F_3$, respectively, are related by the following set of simultaneous equations:

$A_3 = X^2 + X^3$;
$B_3 = X^7$;
$C_3 = 2X^1$;
$D_3 = X^5$;
$E_3 = 2X^1 + X^2$; and or, by solving the above set of equations in terms of $X^1$ to $X^7$:

$X^1 = \frac{1}{2}C_3$;
$X^2 = E_3 - C_3$;
$X^3 = A_3 + C_3 - E_3$;
$X^5 = D_3$;
$X^6 = F_3$; and
$X^7 = B_3$.

Substitution of the values of $a_3$ to $f_3$ as divided by the molecular extinction coefficient 6250 for $A_3$ to $F_3$, respectively, and the molar concentration $x^1$ to $x^7$ of the respective polyamines for the absolute amounts $X^1$ to $X^7$, respectively, in the above set of simultaneous equations gave the values of $x^1$ to $x^7$ as follows:

| | |
| --- | --- |
| $x^1$ for spermine | 40.0 $\mu M$; |
| $x^2$ for spermidine | 39.4 $\mu M$; |
| $x^3$ for putrescine | 39.5 $\mu M$; |
| $x^5$ for $N^1$—acetylspermidine | 40.0 $\mu M$; |
| $x^6$ for $N^8$—acetylspermidine | 38.7 $\mu M$; and |
| $x^7$ for acetylputrescine | 39.2 $\mu M$. |

The above results well coincide with the expected concentration of 40 $\mu M$ for each of the polyamines indicating the high reliability of the inventive method.

EXAMPLE 5

An aqueous mixture was prepared by mixing 1.5 ml of the same coloring solution as used in the step $E_2$ of Example 2, 0.865 ml of distilled water and each 25 μl of 5 aqueous solutions each containing one of the polyamines spermine, spermidine, putrescine and $N^1$- and $N^8$-acetylspermidines in a concentration of 1.0M and the mixture was taken in a 3 ml capacity photometric cell. After a preheating for 3 minutes at 35° C., 5 μl of polyamine oxidase PC-3 corresponding to an amount of about 0.1 unit were added to the mixture to effect the enzymatic reaction and the absorbance of the mixture was measured at a wavelength of 505 nm after about 5 minutes of the reaction time. The concentration of each of the polyamines in this photometric solution was 10 μM as calculated. This procedure is called the step $A_4$.

The aqueous mixture after completion of the step $A_4$ above was further admixed with 5 μl of polyamine oxidase PC-3 corresponding to an amount of about 15 units and the absorbance of the mixture was measured at the same wavelength after about 15 minutes of the reaction time. This procedure following the step $A_4$ is called the step $B_4$.

The aqueous mixture after completion of the above step $B_4$ was further admixed with 10 μl of a 5N aqueous solution of sodium hydroxide to have a pH of 6 to 6.5 and then with 5 μl of polyamine oxidase AT-1 corresponding to an amount of about 5 units to effect the enzymatic reaction followed by the measurement of the absorbance at the same wavelength after about 10 minutes of the reaction time at 35° C. This procedure following the step $B_4$ above is called the step $C_4$.

Separately, another aqueous mixture was prepared by mixing 1.5 ml of the same coloring solution as used in the step $A_2$ of Example 2, 0.830 ml of distilled water and each 25 μl of the same 5 aqueous solutions each containing one of the 5 polyamines as used in the step $A_4$ above followed, after a preheating for 3 minutes at 35° C., by the addition of 5 μl of putrescine oxidase corresponding to an amount of about 5 units to effect the enzymatic reaction. After about 15 minutes of the reaction at 35° C., the aqueous mixture was further admixed with 30 μl of a 5N hydrochloric acid to have a pH of 6 to 6.5 and the absorbance of the aqueous mixture was measured at the same wavelength. This procedure is called the step $D_4$.

The aqueous mixture after completion of the above step $D_4$ was admixed with 5 μl of polyamine oxidase AT-1 corresponding to an amount of about 0.1 unit followed by the measurement of the absorbance at the same wavelength after 10 minutes of the reaction time. This procedure following the step $D_4$ above is called the step $E_4$.

The values of the absorbance or increment of the absorbance $a_4$, $b_4$, $c_4$, $d_4$ and $e_4$ obtained in the above described steps $A_4$ to $E_4$ were 0.188, 0.060, 0.064, 0.124 and 0.125, respectively.

In the above described steps $A_4$ to $E_4$, the molar amounts of the 5 polyamines $X^1$, $X^2$, $X^3$, $X^5$ and $X^6$ for spermine, spermidine, putrescine and $N^1$- and $N^8$-acetylspermidines, respectively, are related to the molar amounts of the hydrogen peroxide $A_4$ to $E_4$ formed in each of the steps $A_4$ to $E_4$, respectively, by the following set of equations:

$A_4 = 2X^1 + X^2$;
$B_4 = X^6$;
$C_4 = X^5$;
$D_4 = X^1 + X^2 + X^3 + X^5$; and
$E_4 = X^2 + X^3$, or, by solving the above equations in terms of $X^1$ to $X^6$, by the set of equations:

$X^1 = D_4 - C_4 - E_4$;
$X^2 = A_4 + 2C_4 + 2E_4 - 2D_4$;
$X^3 = 2D_4 - A_4 - 2C_4 - E_4$;
$X^5 = C_4$; and
$X^6 = B_4$.

Substitution of the values of $a_4$ to $e_4$ as divided by the molecular extinction coefficient 6250 for $A_4$ to $E_4$, respectively, and the molar concentrations $x^1$, $x^2$, $x^3$, $x^5$ and $x^6$ of the respective polyamines for the absolute amounts $X^1$ to $X^6$, respectively, in the above set of simultaneous equations gave the values of $x^1$ to $x^6$ as follows:

| | |
|---|---|
| $x^1$ for spermine | 10.0 μM; |
| $x^2$ for spermidine | 10.1 μM; |
| $x^3$ for putrescine | 10.1 μM; |
| $x^5$ for $N^1$—acetylspermidine | 10.2 μM; and |
| $x^6$ for $N^8$—acetylspermidine | 9.6 μM. |

The above obtained results well coincide with the expected concentration 10.0 μM for each of the polyamines indicating the high reliability of the inventive method.

EXAMPLE 6

This example is given for the case where the concentrations of spermine, spermidine, putrescine and acetylputrescine are to be determined in the analysis of a test sample containing all of the 7 polyamines, i.e. acetylspermine and $N^1$- and $N^8$-acetylspermidines in addition to the above mentioned 4 polyamines.

Aqueous polyamine solutions were prepared each containing one of the above mentioned 7 polyamines available on the market in a concentration of 2.0 mM and an aqueous mixture was prepared in a 3 ml photometric cell by mixing 1.5 ml of the same coloring solution as used in the Standardizing Experiment 1, 0.52 ml of distilled water and each 25 μl of the above prepared 7 polyamine solutions followed, after a preheating for 3 minutes at 35° C., by the addition of 5 μl of polyamine oxidase AT-1 corresponding to an amount of about 0.1 unit. The concentration of each of the polyamines was 20 μM in the final aqueous mixture. After about 5 minutes of the reaction time, the aqueous mixture was further admixed with 0.3 ml of a 0.3M aqueous solution of sodium borate and the absorbance thereof was measured at a wavelength of 505 nm. This procedure is called the step $A_5$.

After completion of the above step $A_5$, the aqueous mixture was admixed with 5 μl of putrescine oxidase corresponding to an amount of about 5 units and the absorbance thereof was measured at the same wavelength after 15 minutes of the reaction time at 35° C. This procedure following the above step $A_5$ is called the step $B_5$.

Separately, another aqueous mixture was prepared by mixing 0.72 ml of distilled water, each 25 μl of the above prepared 7 polyamine solutions and 1.5 ml of a coloring solution prepared by use of a 0.1M phosphate buffer solution having a pH of 7.5 followed, after a preheating for 3 minutes at 35° C., by the addition of 5 μl of acetylputrescine oxidase corresponding to an amount of about 0.5 unit to effect the enzymatic reaction for about 10 minutes. After completion of the reaction, the aqueous mixture was further admixed with 0.1 ml of a 0.3M aqueous solution of sodium borate and the absorbance thereof was measured at a wavelength of 505 nm. This procedure is called the step $C_5$.

After completion of the above step $C_5$, the aqueous mixture was admixed with 5 μl of putrescine oxidase corresponding to an amount of about 5 units and the absorbance thereof was measured at the same wavelength after about 15 minutes of the reaction time. This procedure following the above step $C_5$ is called the step $D_5$.

The values of the absorbance or increment of the absorbance $a_5$, $b_5$, $c_5$ and $d_5$ obtained in the above described steps $A_5$ to $D_5$ were 0.375, 0.374, 0.123 and 0.250, respectively.

In the above described steps $A_5$ to $D_5$, the molar amounts of the 4 polyamines $X^1$, $X^2$, $X^3$ and $X^7$ for spermine, spermidine, putrescine and acetylputrescine, respectively, are related to the molar amounts of the hydrogen peroxide $A_5$ to $D_5$ formed in the steps $A_5$ to $D_5$, respectively, by the following set of equations:

$X^1 = B_5 - D_5$;
$X^2 = A_5 + 2D_5 - 2B_5$;
$X^3 = 2B_5 - A_5 - D_5$; and
$X^7 = E_5$.

Substitution of the values of $a_5$ to $d_5$ as divided by the molecular extinction coefficient 6250 for $A_5$ to $D_5$, respectively, and the molar concentrations of the respective polyamines $x^1$, $x^2$, $x^3$ and $x^7$ for $X^1$, $X^2$, $X^3$ and $X^7$, respectively, in the above set of equations gave the values of them as follows:

| | |
|---|---|
| $x^1$ for spermine | 19.8 μM; |
| $x^2$ for spermidine | 20.3 μM; |
| $x^3$ for putrescine | 19.7 μM; and |
| $x^7$ for acetylputrescine | 19.7 μM. |

The above obtained results well coincide with the expected concentration of 20.0 μM for each of the polyamines indicating the high reliability of the inventive method.

EXAMPLE 7

This example is given for the case where the concentrations of spermine, spermidine, putrescine and $N^8$-acetylspermidine are to be determined in the analysis of a test sample containing all of the 7 polyamines, i.e. acetylspermine, $N^1$-acetylepermidine and acetylputrescine in addition to the above mentioned 4 polyamines.

Steps $A_6$ and $B_6$ were undertaken each in the same manner as in the steps $A_1$ and $B_1$ in Example 1, respectively.

Separately, another aqueous mixture was prepared by mixing 0.75 ml of distilled water, each 25 μl of the same 7 polyamine solutions as used in Example 1 and 1.5 ml of a coloring solution prepared with the same formulation as above excepting the use of a buffer solution which was a 1:1 by volume mixture of a 0.1M phosphate buffer solution having a pH of 8.5 and a 0.1M sodium carbonate/potassium chloride/boric acid buffer solution having a pH of 8.5 in place of the buffer solution having a pH of 6.5. After a preheating for 3 minutes at 35° C., the aqueous mixture was admixed with 5 μl of putrescine oxidase corresponding to an amount of about 5 units to effect the enzymatic reaction for about 15 minutes followed by the addition of 40 μl of a 5N hydrochloric acid and measurement of the absorbance at a wavelength of 505 nm. This procedure is called the step $C_6$.

The aqueous mixture after completion of the above step $C_6$ was admixed with 5 μl of polyamine oxidase PC-3 corresponding to an amount of about 15 units and the absorbance thereof was measured at the same wavelength after about 10 minutes of the reaction time. This procedure following the above step $C_6$ is called the step $D_6$.

The values of the absorbance or increment of the absorbance $a_6$, $b_6$, $c_6$ and $d_6$ obtained in the above described steps $A_6$ to $D_6$ were 0.375, 0.375, 0.250 and 0.370, respectively.

In the above described steps $A_6$ to $D_6$, the molar amounts of the 4 polyamines $X^1$, $X^2$, $X^3$ and $X^6$ for spermine, spermidine, putrescine and $N^8$-acetylspermidine, respectively, are related to the molar amounts of hydrogen peroxdie $A_6$ to $D_6$ formed in the steps $A_6$ to $D_6$, respectively, by the following set of equations:

$X^1 = B_6 - C_6$;
$X^2 = A_6 + 2C_6 - 2B_6$;
$X^3 = 2B_6 - A_6 - C_6$; and
$X^6 = 2C_6 + D_6 - 2B_6$.

Substitution of the values of $a_6$ to $d_6$ as divided by the molecular extinction coefficient 6250 for $A_6$ to $D_6$, respectively, and the molar concentrations of the respective polyamines $x^1$, $x^2$, $x^3$ and $x^6$ for $X^1$, $X^2$, $X^3$ and $X^6$, respectively, in the above set of equations gave the values of them as follows:

| | |
|---|---|
| $x^1$ for spermine | 20.0 μM; |
| $x^2$ for spermidine | 20.0 μM; |
| $x^3$ for putrescine | 20.0 μM; and |
| $x^6$ for $N^8$—acetylspermidine | 19.2 μM. |

The above obtained results well coincide with the expected concentration of 20.0 μM for each of the polyamines indicating the high reliablity of the inventive method.

EXAMPLE 8

An aqueous mixture was prepared in a 3 ml photometric cell by mixing 1.5 ml of the same coloring solution as used in the Standardizing Experiment 1, 0.50 ml of distilled water and each 25 μl of 4 polyamine solutions each containing one of the polyamines acetylspermine, $N^1$- and $N^8$-acetylspermidines and acetylputrescine in a concentration of 2.0 mM. The concentration of each of the polyamines in the final aqueous mixture was 20 μM. After a preheating for 3 minutes at 35° C., the aqueous mixture was admixed with 5 μl of polyamine oxidase AT-1 corresponding to an amount of about 5 units to effect the enzymatic reaction for 10 minutes followed by the addition of 0.3 ml of a 0.3M aqueous solution of sodium borate and measurement of the absorbance at a wavelength of 505 nm. This procedure is called the step $A_7$.

After completion of the above step $A_7$, the aqueous mixture was admixed with 5 μl of putrescine oxidase corresponding to an amount of about 5 units and the absorbance thereof was measured at the same wavelength after 15 minutes of the reaction at 35° C. This procedure following the above step $A_7$ is called the step $B_7$.

Separately, another aqueous mixture was prepared in a 3 ml photometric cell by mixing each 25 μl of the same 4 polyamine solutions as used in the step $A_7$, 1.5 ml of the coloring solution prepared by use of a 0.1M phosphate buffer solution having a pH of 5.5 and 0.84 ml of distilled water followed, after a preheating for 3 minutes at 35° C., by the addition of 5 μl of polyamine oxidase PC-3 corresponding to an amount of about 15 units to effect the enzymatic reaction. After about 15 minutes of the reaction time, the aqueous mixture was admixed with 50 μl of a 5N aqueous solution of sodium hydroxide to have a pH of about 7.5 and the absorbance thereof was measured at a wavelength of 505 nm. This procedure is called the step $C_7$.

After completion of the above step $C_7$, the aqueous mixture was admixed with 5 μl of acetylputrescine oxidase corresponding to an amount of about 0.5 unit and the absorbance thereof was measured at the same wavelength after about 10 minutes of the reaction time. This procedure following the above step $C_7$ is called the step $D_7$. The increment of the absorbance in this step $D_7$ is due to the hydrogen peroxide formed from the acetylputrescine in the starting solution and the acetylputrescine as the product in the oxidation of the $N^8$-acetylspermidine in the preceding step $C_7$.

The values of the absorbance or increment of the absorbance $a_7$, $b_7$, $c_7$ and $d_7$ obtained in the above described steps $A_7$ to $D_7$ were 0.375, 0.250, 0.130 and 0.262, respectively.

In the above described steps $A_7$ to $D_7$, the molar amounts of the 4 polyamines $X^4$, $X^5$, $X^6$ and $X^7$ for acetylspermine, $N^1$- and $N^8$-acetylspermidines and acetylputrescine, respectively, are related to the molar amounts of the hydrogen peroxide $A_7$ to $D_7$ formed in the steps $A_7$ to $D_7$, respectively, by the following set of equations:

$A_7 = 2X^4 + X^5$;
$B_7 = X^4 + X^5$,
$C_7 = X^6$; and
$D = X^6 + X^7$, or, by solving the above set of equations in terms of $X^4$ to $X^7$, by the set of equations:

$X^4 = A_7 - B_7$;
$X^5 = 2B_7 - A_7$;
$X^6 = C_7$; and
$X^7 = D_7 - C_7$.

Substitution of the values of $a_7$ to $d_7$ as divided by the molecular extinction coefficient 6250 for $A_7$ to $D_7$, respectively, and the molar concentrations of the respective polyamines $x^4$ to $x^7$ for $X^4$ to $X^7$, respectively, in the above set of equations gave the values of them as follows:

| | |
|---|---|
| $x^4$ for acetylspermine | 20.0 μM; |
| $x^5$ for $N^1$—acetylspermidine | 20.0 μM; |
| $x^6$ for $N^8$—acetylspermidine | 20.8 μM; and |
| $x^7$ for acetylputrescine | 21.1 μM. |

The above obtained results well coincide with the expected concentration of 20.0 μM for each of the polyamines indicating the high reliability of the inventive method.

EXAMPLE 9

An aqueous mixture was prepared in a 3 ml photometric cell by mixing 1.5 ml of the same coloring solution as used in the Standardizing Experiment 1, 0.54 ml of distilled water and each 50 μl of 3 polyamine solutions each containing one of the polyamines acetylspermine and $N^1$- and $N^8$-acetylspermidines in a concentration of 1.0 mM. The concentration of each of the polyamines in the final aqueous mixture was 20 μM. After a preheating for 3 minutes at 35° C., the aqueous mixture was admixed with 5 μl of polyamine oxidase AT-1 corresponding to an amount of about 3 units to effect the enzymatic reaction for 10 minutes and then with 0.3 ml of a 0.3M aqueous solution of sodium borate followed by the measurement of the absorbance at a wavelength of 505 nm. This procedure is called the step $A_8$.

After completion of the above step $A_8$, the aqueous mixture was further admixed with 5 μl of putrescine oxidase corresponding to an amount of about 5 units to effect the enzymatic reaction for 15 minutes at 35° C. followed by the measurement of the absorbance at the same wavelength. This procedure following the above step $A_8$ is called the step $B_8$.

After completion of the above step $B_8$, the aqueous mixture was further admixed with 50 μl of a 5N hydrochloric acid to have a pH of about 5.5 and then with 5 μl of polyamine oxidase PC-3 corresponding to an amount of about 15 units followed by the measurement of the absorbance at the same wavelength after about 15 minutes of the reaction time. This procedure following the above step $B_8$ is called the step $C_8$.

The values of the absorbance or increment of the absorbance $a_8$, $b_8$ and $c_8$ obtained in the above described steps $A_8$ to $C_8$ were 0.370, 0.250 and 0.129, respectively.

In the above described steps $A_8$ to $C_8$, the molar amounts of the 3 polyamines $X^4$, $X^5$ and $X^6$ for acetylspermine and $N^1$- and $N^8$-acetylspermidines, respectively, are related to the molar amounts of the hydrogen peroxide $A_8$, $B_8$ and $C_8$ formed in the steps $A_8$ to $C_8$, respectively, by the following set of equations:

$A_8 = 2X^4 + X^5$;
$B_8 = X^4 + X^5$; and
$C_8 = X^6$, or, by solving the above set of equations in terms of $X^4$ to $X^6$, by the set of equations:

$X^4 = A_8 - B_8$;
$X^5 = 2B_8 - A_8$; and
$X^6 = C_8$.

Substitution of the values of $a_8$ to $c_8$ as divided by the molecular extinction coefficient 6250 for $A_8$ to $C_8$, respectively, and the molar concentrations of the respective polyamines $x^4$, $x^5$ and $x^6$ for $X^4$ to $X^6$, respectively, in the above set of equations gave the values of them as follows:

| | |
|---|---|
| $x^4$ for acetylspermine | 19.2 μM; |
| $x^5$ for $N^1$—acetylspermidine | 20.8 μM; and |
| $x^6$ for $N^8$—acetylspermidine | 20.6 μM. |

The above obtained results well coincide with the expected concentration of 20.0 μM for each of the polyamines indicating the high reliability of the inventive method.

EXAMPLE 10

A coloring solution was prepared with the same formulation as in the Standardizing Experiment 1 but with the use of a 0.1M phosphate buffer solution having a pH of 5.5 and an aqueous mixture was prepared in a 3 ml photometric cell by mixing 1.5 ml of the above prepared coloring solution, 0.84 ml of distilled water and each 50 μl of 2 polyamine solutions each containing $N^8$-acetylspermindine or acetylputrescine in a concentration of 2.0 mM. The concentration of each of the above polyamines in the final aqueous mixture was 40 μM.

After a preheating for 3 minutes at 35° C., the aqueous mixture was admixed with 5 μl of polyamine oxidase PC-3 corresponding to an amount of about 15 units to effect the enzymatic reaction for 15 minutes and then with 50 μl of a 5N aqueous solution of sodium hydroxide to have a pH of about 7.5 followed by the measurement of the absorbance thereof at a wavelength of 505 nm. This procedure is called the step $A_9$.

After completion of the above step $A_9$, the aqueous mixture was further admixed with 5 μl of acetylputrescine oxidase corresponding to an amount of about 0.5 unit and the absorbance thereof was measured at the same wavelength after about 10 minutes of the reaction time. This procedure following the above step $A_9$ is called the step $B_9$.

The values of the absorbance or increment of the absorbance $a_9$ and $b_9$ obtained in the above described steps $A_9$ and $B_9$ were 0.252 and 0.508, respectively.

In the above described steps $A_9$ and $B_9$, the molar amounts of the $N^8$-acetylspermidine and acetylputrescine $X^6$ and $X^7$, respectively, are related to the molar amounts of the hydrogen peroxide $A_9$ and $B_9$ formed in the steps $A_9$ and $B_9$, respectively, by the following set of equations:

$A_9 = X^6$; and
$B_9 = X^6 + X^7$, or, by solving the above set of equations in terms of $X^6$ and $X^7$, by the set of equations:

$X^6 = A_9$; and
$X^7 = B_9 - A_9$.

Substitution of the values of $a_9$ and $b_9$ as divided by the molecular extinction coefficient 6250 for $A_9$ and $B_9$, respectively, and the molar concentrations of the respective polyamines $x^6$ and $x^7$ for $X^6$ and $X^7$, respectively, in the above set of equations gave the values of them as follows:

| | |
|---|---|
| $x^6$ for $N^8$—acetylspermidine | 40.3 μM; and |
| $x^7$ for acetylputrescine | 41.0 μM. |

The above obtained results are in good approximation with the expected concentration of 40.0 μM for each of polyamines indicating the high reliability of the inventive method.

EXAMPLE 11

This example describes an alternative for the analysis of the human urine analyzed in the preceding Example 2.

Thus, a coloring solution was prepared with the same formulation as in Example 2 but by use of a 0.1M phosphate buffer solution having a pH of 6.5 in place of the buffer solution having a pH of 8.5 and an aqueous mixture was prepared by mixing 1.5 ml of the above prepared coloring solution, 0.5 ml of the urine and 0.19 ml of distilled water. After a preheating for 3 minutes at 35° C., the aqueous mixture was admixed with 10 μl of polyamine oxidase AT-1 corresponding to an amount of 0.1 unit to effect the enzymatic reaction for 5 minutes and then with 0.3 ml of a 0.3M aqueous solution of sodium borate to have a pH of about 8 and a total liquid volume of 2.5 ml followed by the measurement of the absorbance at a wavelength of 555 nm. This procedure is called the step $A_{10}$.

After completion of the above step $A_{10}$, the aqueous mixture was admixed with 5 μl of putrescine oxidase corresponding to an amount of 5 units to effect the enzymatic reaction for 15 minutes at 35° C. followed by the measurement of the absorbance thereof at the same wavelength as above. This procedure following the above step $A_{10}$ is called the step $B_{10}$.

Separately, another aqueous mixture was prepared by mixing 1.5 ml of the same coloring solution as used in Example 2, 0.5 ml of the urine and 0.495 ml of distilled water followed, after a preheating for 3 minutes at 35° C., by the addition of 5 μl of putrescine oxidase corresponding to an amount of 5 units to effect the enzymatic reaction for 15 minutes at 35° C. followed by the measurement of the absorbance thereof at a wavelength of 555 nm. This procedure is called the step $C_{10}$.

Another 20 ml portion of the same urine was acidified by adding 5.0 ml of 12N hydrochloric acid and heated at 100° C. for 3 hours. The precipitates formed there were removed by centrifugal separation and a 10N aqueous solution of sodium hydroxide was added to the clear solution to give a pH of about 6. This solution was diluted by adding 60 ml of distilled water to have a total volume of about 100 ml and passed through a column of 2.0 ml volume filled with Amberlite CG-50 resin to cause adsorption of the ingredients thereon followed by washing of the resin with 20 ml of distilled water and 3 ml of a 0.5N hydrochloric acid. Thereafter, elution of the resin in the column was undertaken with 10 ml of a 0.5N hydrochloric acid and the eluate solution was neutralized to have a pH of about 7 by use of a 10N aqueous solution of sodium hydroxide and diluted with distilled water to a total volume of 20 ml. This solution is called the deacetylated urine solution and was used in the following steps.

An aqueous mixture was prepared by mixing 0.5 ml of the above obtained deacetylated urine solution, 1.5 ml of the same coloring solution as used in the step $A_{10}$ above and 0.19 ml of distilled water followed, after a preheating for 3 minutes at 35° C., by the addition of 10 μl of polyamine oxidase AT-1 corresponding to an amount of 0.1 unit to effect the enzymatic reaction. After 5 minutes of the reaction at 35° C., the aqueous mixture was admixed with 0.3 ml of a 0.3M aqueous solution of sodium borate and the absorbance thereof was measured at a wavelength of 555 nm. This procedure is called the step $D_{10}$.

The aqueous mixture after completion of the above step $D_{10}$ was admixed with 5 μl of putrescine oxidase corresponding to an amount of 5 units and the absorbance thereof was measured after 15 minutes of the reaction time at 35° C. This procedure following the above step $D_{10}$ is called the step $E_{10}$.

Further separately, another aqueous mixture was prepared by mixing 1.5 ml of the same coloring solution as used in the ste $C_{10}$ above, 0.5 ml of the deacetylated urine solution and 0.495 ml of distilled water followed, after a preheating for 3 minutes at 35° C., by the addition of 5 μl of putrescine oxidase corresponding to an amount of about 5 units to effect the enzymatic reaction and the absorbance thereof was measured at a wavelength of 555 nm after 15 minutes of the reaction time at 35° C. This procedure is called the step $F_{10}$.

The values of the absorbance or increment of the absorbance obtained in the above described steps $A_{10}$ to $F_{10}$ were 0.027, 0.033, 0.025, 0.042, 0.081 and 0.073, respectively.

By setting up a set of simultaneous equations to give the relationship between the molar concentration of each of the polyamines spermine, spermidine, putrescine, acetylspermine, acetylspermidine and acetylputrescine and the above given values of the absorbance as divided by the molecular extinction coefficient 17,200 and solving the equations, the molar concentrations of the polyamines in the photometric solutions were obtained, which could be converted to the molar concentrations of the polyamines in the urine. The results are as tabulated below.

| Polyamine | Concentration in the photometric solution, $\mu M$ | Concentration in the urine, $\mu M$ |
|---|---|---|
| Spermine | 0.47 | 2.4 |
| Spermidine | 0.64 | 3.2 |
| Putrescine | 0.81 | 4.1 |
| Acetylspermine | 0 | 0 |
| Acetylspermidine* | 0.87 | 4.4 |
| Acetylputrescine | 1.90 | 9.5 |

*Total amount of $N^1$— and $N^8$—acetylspermidines.

The results are in good coincidence with the results obtained in Example 2 indicating the high reliability of each of the procedures in these examples.

What is claimed is:

1. A method for the quantitative determination of the individual contents of polyamine components in an aqueous mixture containing at least one of the polyamines selected from the group consisting of free polyamines including spermine, spermidine and putrescine and acetylated polyamines including acetylspermine, $N^1$- and $N^8$-acetylspermidines and acetylputrescine, of which at least one is one of the said acetylated polyamines, which comprises the steps of:
   (a) subjecting the aqueous mixture to at least two steps of enzymatic oxidative decomposition reactions successively or separately, the number of the reaction steps being the same as or larger than the number of the polyamine components in the aqueous mixture, each by use of an oxidation enzyme selected from the group consisting of polyamine oxidases, putrescine oxidase and acetylputrescine oxidase, the kind of the enzyme or the conditions of the reaction being effective for the enzymatic oxidative decomposition of one or several of the polyamines but ineffective for the other polyamine components, to form hydrogen peroxide as a byproduct of the enzymatic oxidative decomposition reaction,
   (b) determining the amount of the hydrogen peroxide formed in each of the steps of the enzymatic oxidative decomposition reactions,
   (c) setting up a set of simultaneous equations each giving the amount of the hydrogen peroxide formed in each of the reaction steps as a function of the contents of the individual polyamine components in the aqueous mixture, and
   (d) solving the simultaneous equations in terms of the respective contents of the individual polyamine components in the aqueous mixture.

2. The method as claimed in claim 1 wherein the polyamine oxidases are polyamine oxidase AT-1 and polyamine oxidase PC-3.

3. The method as claimed in claim 1 wherein the determination of the amount of hydrogen peroxide in the step (b) is carried out photometrically.

4. The method as claimed in claim 1 wherein the step (a) is carried out by the sequence or combination of the steps comprising:
   (A) subjecting a first portion of the aqueous mixture to the oxidative decomposition reaction in the presence of a polyamine oxidase in such a concentration that spermine and spermidine are decomposed,
   (B) subjecting the aqueous mixture after the step (A) to the oxidative decomposition reaction in the presence of putrescine oxidase,
   (C) subjecting a second portion of the aqueous mixture to the oxidative decomposition reaction in the presence of the polyamine oxidase in such a concentration that spermine, spermidine, acetylspermine and $N^1$-acetylspermidine are decomposed,
   (D) subjecting the aqueous mixture after the step (C) to the oxidative decomposition reaction in the presence of putrescine oxidase,
   (E) subjecting a third portion of the aqueous mixture to the oxidative decomposition reaction in the presence of putrescine oxidase,
   (F) subjecting the aqueous mixture after the step (E) to the oxidative decomposition reaction in the presence of acetylputrescine oxidase, and
   (G) subjecting the aqueous mixture after the step (F) to the oxidative decomposition reaction in the presence of a polyamine oxidase reactive on $N^8$-acetylspermidine.

5. The method as claimed in claim 1 wherein the step (a) is carried out by the sequence or combination of the steps comprising:
   (A) subjecting a first portion of the aqueous mixture to the oxidative decomposition reaction in the presence of putrescine oxidase,
   (B) subjecting the aqueous mixture after the step (A) to the oxidative decomposition reaction in the presence of a polyamine oxidase in such a concentration and at such a condition of pH that spermine is decomposed,
   (C) subjecting the aqueous mixture after the step (B) to the oxidative decomposition reaction in the presence of a polyamine oxidase reactive on $N^1$-acetylspermidine and acetylspermine in such a concentration that $N^1$-acetylspermidine and acetylspermine are decomposed,
   (D) subjecting the aqueous mixture after the step (C) to the oxidative decomposition reaction at such a modified condition of pH that putrescine is decomposed by the reactivation of the putrescine oxidase added in the step (A),
   (E) subjecting a second portion of the aqueous mixture to the oxidative decomposition reaction in the presence of a polyamine oxidase, which may be the same as or different from the polyamine oxidase used in the step (B), in such a concentration that spermine and spermidine are decomposed,
   (F) subjecting the aqueous mixture after the step (E) to the oxidative decomposition reaction in the presence of a polyamine oxidase reactive on $N^8$-acetylspermidine in such a concentration that $N^8$-acetylspermidine is decomposed, and
   (G) subjecting the aqueous mixture after the step (F) to the oxidative decomposition reaction in the presence of acetylputrescine oxidase.

6. The method as claimed in claim 4 wherein the polyamine oxidase used in the step (A) is polyamine oxidase AT-1.

7. The method as claimed in claim 4 wherein the polyamine oxidase reactive on $N^8$-acetylspermidine used in the step (G) is polyamine oxidase PC-3.

8. The method as claimed in claim 5 wherein the polyamine oxidase used in the steps (B) and (E) is polyamine oxidase AT-1 or polyamine oxidase PC-3.

9. The method as claimed in claim 5 wherein the polyamine oxidase reactive on $N^1$-acetylspermidine and acetylspermine used in the step (C) is polyamine oxidase AT-1.

10. The method as claimed in claim 5 wherein the polyamine oxidase reactive on $N^8$-acetylspermidine used in the step (F) is polyamine oxidase PC-3.

* * * * *